United States Patent

Ishiguro et al.

[11] Patent Number: 6,051,569
[45] Date of Patent: Apr. 18, 2000

[54] 1'S, 5R, 6R-CARBAPENEM DERIVATIVES AND ANTIMICROBIAL AGENTS COMPRISING THE SAME

[75] Inventors: Masaji Ishiguro, Takarazuka; Takashi Nakatsuka, Mishima-gun; Hidekazu Inoue, Ibaraki, all of Japan

[73] Assignee: Suntory Limited, Osaka, Japan

[21] Appl. No.: 08/911,937

[22] Filed: Aug. 15, 1997

[30] Foreign Application Priority Data

Aug. 16, 1996 [JP] Japan ................................. 8-233676

[51] Int. Cl.[7] .......................... A61K 31/40; C07D 477/20
[52] U.S. Cl. ............................................. 514/210; 540/350
[58] Field of Search .............................. 514/210; 540/350

[56] References Cited

U.S. PATENT DOCUMENTS

| | | | |
|---|---|---|---|
| 4,374,144 | 2/1983 | Corbett | 424/274 |
| 4,387,051 | 6/1983 | Corbett et al. | 260/245.25 |
| 4,410,533 | 10/1983 | Ponsford et al. | 424/251 |
| 4,413,000 | 11/1983 | Eglington | 424/269 |
| 4,477,662 | 10/1984 | Corbett et al. | 260/245.27 |
| 4,683,226 | 7/1987 | McCombie | 540/310 |
| 4,997,829 | 3/1991 | Ishiguro et al. | 514/310 |
| 5,116,832 | 5/1992 | Ishiguro et al. | 514/310 |

FOREIGN PATENT DOCUMENTS

| | | |
|---|---|---|
| 0 061 231 | 9/1982 | European Pat. Off. |
| 0 773 222 | 5/1997 | European Pat. Off. |

OTHER PUBLICATIONS

Yoshihiro Sumita, et al.: "Antimicrobial Activity of SM–17466, a Novel Carbapenem Antibiotic with Potent Activity against Methicillin–Resistant *Staphylococcus aureus*", Antinmicrobial Agents and Chemotherapy, vol. 39, No. 4, Apr. 1994, pp. 910–916.

Database WPI; Section Ch, Week 9617; Derwent Publications Ltd., London, GB; Class B02, AN 96–171546; XP002049266 (1996).

*Primary Examiner*—Mark L. Berch
*Attorney, Agent, or Firm*—Oblon, Spivak, McClelland, Maier & Neustadt, P.C.

[57] ABSTRACT

A carbapenem derivative represented by the following formula (I),

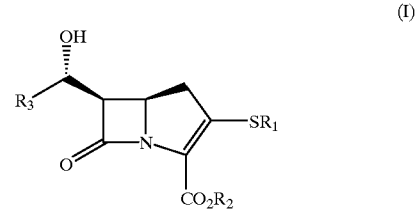

wherein $R_1$ represents a hydrogen atom, a substituted or unsubstituted aryl group, or a substituted or unsubstituted heterocyclic group, $R_2$ indicates a hydrogen atom or a protective group for a carboxyl group, and $R_3$ is a methyl group or an ethyl group; or a pharmaceutically acceptable salt thereof, and a pharmaceutical composition comprising this carbapenem derivative or a salt thereof as an active ingredient. The carbapenem derivative exhibits a wide and strong antimicrobial activity, particularly a strong antimicrobial activity against MRSA. An intermediate compound for preparing the carbapenem derivative is also disclosed.

11 Claims, No Drawings

6,051,569

1'S, 5R, 6R-CARBAPENEM DERIVATIVES AND ANTIMICROBIAL AGENTS COMPRISING THE SAME

BACKGROUND OF THE INVENTION

1. Field of the Invention

The present invention relates to a novel carbapenem derivative and, more specifically, to a carbapenem derivative exhibiting an antimicrobial activity against various microorganisms, particularly against methicillin-resistant *Staphylococcus aureus* (MRSA) which has recently been identified as a cause of hospital acquired infection, and useful not only as a medicine for human beings but also in veterinary medicine. The present invention also relates to a pharmaceutical composition, particularly to an antimicrobial agent, comprising this carbapenem derivative as an effective component.

2. Description of the Background Art

A number of studies have been undertaken about carbapenem type antibiotics because of their possession of strong and broad antimicrobial activities. These studies have confirmed that the antimicrobial activities of carbapenem compounds largely differ according to three asymmetrical carbon atoms 1', 5, and 6 on the basic carbapenem molecular structure shown below, that is, a combination of the configuration for these three carbon atoms, and also to the kind of substituent on the position 2 (for example, "β-Lactam-based medicines" (Nankodo, 1987), pp 664–685, coedited by UEDA and SHIMIZU).

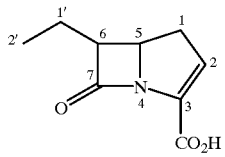

The carbapenem compounds with the configuration (1'R, 5R,6S) is known to exhibit the strongest activity (e.g., "β-Lactam-based medicines" (Nankodo, 1987), pp 664–685, coedited by UEDA and SHIMIZU). Most carbapenem compounds currently known have this configuration.

Several naturally occurring carbapenem compounds with the configuration (1'S,5R,6R) are also known in the art (e.g., Chemistry and Biology of β-lactam Antibiotics, Vol. 2 (1982), pp 227–251, Eds. R. B. Morin and M. Gorman, Academic Press, New York). The activity of these naturally occurring carbapenem compounds is not so strong as that of the carbapenem compounds with the configuration (1'R,5R, 6S).

Therefore, only replacement of the substituent on the position 2 has been considered to be effective for improving the activity of carbapenem compounds.

Ineffectiveness of almost all conventional antibiotics against high resistant MRSA (methicillin-resistant *Staphylococcus aureus*), the incidence of which is expected to increase, is a big issue. Development of antibiotics which are effective against both the MRSA and other many conventionally known bacteria has been strongly desired.

The present inventors have undertaken extensive studies paying attention to carbapenem compounds to discover a compound possessing a powerful antimicrobial activity against a wide variety of microorganisms. The present inventors have synthesized a great number of carbapenem derivatives, while paying attention particularly to the configuration of the 6 position substituent, the configuration on the β-lactam ring, and the 2 position substituent of carbapenem compounds, and have examined the antimicrobial activities of the synthesized carbapenem derivatives and conventionally known carbapenem derivatives.

As a result, the present inventors have found that carbapenem derivatives possessing specific substituents and specific configurations exhibit strong antimicrobial activity against a wide variety of microorganisms, particularly against MRSA. This finding has led to the completion of the present invention.

SUMMARY OF THE INVENTION

Accordingly, an object of the present invention is to provide a carbapenem derivative represented by the following formula (I),

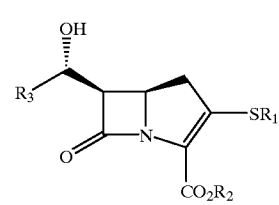

(I)

wherein $R_1$ represents a hydrogen atom, a substituted or unsubstituted aryl group, or a substituted or unsubstituted heterocyclic group, $R_2$ indicates a hydrogen atom or a protective group for a carboxyl group, and $R_3$ is a methyl group or an ethyl group; or a pharmaceutically acceptable salt thereof.

Another object of the present invention is to provide a pharmaceutical composition, particularly an antimicrobial agent, comprising a carbapenem derivative represented by the following formula (I),

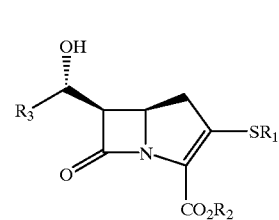

(I)

wherein $R_1$, $R_2$, and $R_3$ are the same as defined above, or a pharmaceutically acceptable salt thereof as an effective component.

Still another object of the present invention is to provide a compound of the following formula (II),

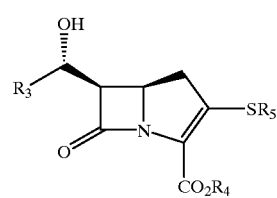

(II)

wherein $R_4$ indicates a protective group for a carboxyl group; $R_5$ represents a substituted or unsubstituted alkyl group, a substituted or unsubstituted alkenyl group, a substituted or unsubstituted aralkyl group, a substituted or unsubstituted aryl group, a substituted or unsubstituted heterocyclic group, or a substituted or unsubstituted acyl group; and $R_3$ is the same as defined above; and a compound of the following formula (III),

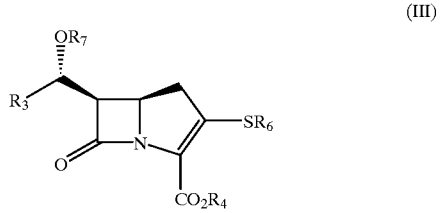

(III)

wherein $R_6$ represents a substituted or unsubstituted alkyl group, a substituted or unsubstituted alkenyl group, a substituted or unsubstituted aralkyl group, a substituted or unsubstituted aryl group, a substituted or unsubstituted heterocyclic group, or a substituted or unsubstituted acyl group; $OR_7$ indicates a protected hydroxyl group; and $R_3$ and $R_4$ are the same as defined above; both compounds being useful as intermediates for synthesizing the carbapenem derivative of formula (I).

Other objects, features and advantages of the invention will hereinafter become more readily apparent from the following description.

DETAILED DESCRIPTION OF THE INVENTION AND PREFERRED EMBODIMENTS

In the carbapenem derivative (I), compound (II), and compound (III) of the present invention, preferred examples for the aryl group of $R_1$ and the alkyl group, alkenyl group, aralkyl group, and aryl group of $R_5$ and $R_6$ are as follows.

First, given as examples of alkyl group are linear or branched lower alkyl groups such as a methyl group, ethyl group, n-propyl group, isopropyl group, n-butyl group, tert-butyl group, and hexyl group; and monocyclic or polycyclic alkyl groups which may form a condensed ring with an aromatic hydrocarbon, such as a cyclopentyl group, cyclohexyl group, menthyl group, fenchyl group, bornyl group, and indanyl group. These may include a carbonyl group in the chain or ring. Next, as examples of the alkenyl group, linear or branched lower alkenyl groups such as a vinyl group, allyl group, 1-propenyl group, 2-butenyl group, and 2-methyl-2-propenyl group are given.

In this specification, unless otherwise specified "lower" preferably means a carbon atom number of 1–6, particularly 1–4.

Next, given as examples of the aralkyl group are aralkyl groups having 7–24 carbon atoms, such as a benzyl group, phenethyl group, 3-phenylpropyl group, 2-naphthylmethyl group, 2-(1-naphthyl)ethyl group, trityl group, and benzhydryl group. As examples of the aryl group are an aryl group having 6–10 carbon atom, such as a phenyl group and naphthyl group.

These alkyl groups, alkenyl groups, aralkyl groups, and aryl groups may be replaced by one or more substituents.

Given as examples of such substituents are halogen atoms such as fluorine atom, chlorine atom, and bromine atom; carboxyl group; thiocarboxyl group; formyl group; nitro group; cyano group; hydroxyl group; amino group; linear or branched lower alkyl group such as methyl group, ethyl group, n-propyl group, isopropyl group, n-butyl group, tert-butyl group, and n-hexyl group; mono- or polycyclic alkyl group such as cyclopentyl group, cyclohexyl group, menthyl group, fenchyl group, bornyl group; linear or branched lower alkenyl group such as vinyl group, allyl group, 1-propenyl group, 2-butenyl group, and 2-methyl-2-propenyl group; aryl group having 6–10 carbon atoms such as phenyl group and naphthyl group; and aralkyl group having 7–24 carbon atoms such as benzyl group, phenethyl group, trityl group, and benzhydryl group.

Given as further examples of the substituents are alkylthio groups, alkenylthio groups, aralkylthio groups, arylthio groups, alkyloxy groups, alkenyloxy groups, aralkyloxy groups, and aryloxy groups, each corresponding to the above-mentioned alkyl groups, alkenyl groups, aralkyl groups, and aryl groups; alkyl sulfinyl groups and alkyl sulfonyl groups corresponding to the above-mentioned alkyl groups; aralkyl sulfinyl groups and aralkyl sulfonyl groups corresponding to the above-mentioned aralkyl groups; aryl sulfinyl groups and aryl sulfonyl groups corresponding to the above-mentioned aryl groups; amino sulfonyl groups; carbamoyl group; carbamoyloxy group; carbamoyl alkyl groups; imino lower alkyl groups; imino lower alkyl amino groups; acyloxy groups and acyl alkyl groups corresponding to the below-mentioned acyl groups; and the below-mentioned silyloxy groups, heterocyclic groups, heterocyclic-thio groups, heterocyclic-oxy groups, acyl groups, esterified carboxyl groups, and esterified thiocarboxyl groups.

These substitution groups may further be substituted by one or more substituents such as, for example, the above-described substitution groups. Given as specific examples of such additional substituents for the above-mentioned substitution alkyl groups (the same applies to the above-mentioned alkylthio groups, alkyloxy groups, alkyl sulfinyl groups, and alkyl sulfonyl groups) are halogen atoms, a carboxyl group, thiocarboxyl group, formyl group, nitro group, cyano group, hydroxyl group, amino group, alkenyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, imino group, imino lower alkyl amino groups, acyloxy groups, silyloxy groups, heterocyclic groups, heterocyclic-thio groups, heterocyclic-oxy groups, acyl groups, esterified carboxyl groups, and esterified thiocarboxyl groups.

Given as examples of such additional substituents for the above-mentioned substitution alkenyl groups (the same applies to the alkenylthio groups, alkenyloxy groups) are halogen atoms, a carboxyl group, thiocarboxyl group, formyl group, nitro group, cyano group, hydroxyl group, amino group, alkyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyl oxy group, carbamoyl alkyl groups, imino lower alkyl groups, imino lower alkyl amino groups, acyloxy groups, acyl alkyl groups, silyloxy groups, heterocyclic groups, heterocyclic-thio groups, heterocyclic-oxy groups, acyl groups, esterified carboxyl groups, and esterified thiocarboxyl groups.

Further, given as examples of such additional substituents for the above-mentioned substitution aralkyl groups (the same applies to the aralkylthio groups, aralkyloxy groups, aralkyl sulfinyl groups, and aralkyl sulfonyl groups) are halogen atoms, a carboxyl group, thiocarboxyl group, formyl group, nitro group, cyano group, hydroxyl group, amino group, alkyl groups, alkenyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, carbamoyl alkyl groups, imino lower alkyl groups, imino lower alkyl amino groups, acyloxy groups, acyl alkyl groups, silyloxy groups, heterocyclic groups, heterocyclic-thio groups, heterocyclic-oxy groups, acyl groups, esterified carboxyl groups, and esterified thiocarboxyl groups.

Given as examples of such additional substituents for the above-mentioned substitution aryl groups (the same applies to the arylthio groups, aryloxy groups, aryl sulfinyl groups, and aryl sulfonyl groups) are halogen atoms, a carboxyl group, thiocarboxyl group, formyl group, nitro group, cyano group, hydroxyl group, amino group, alkyl groups, alkenyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, carbamoyl alkyl groups, imino lower alkyl groups, imino lower alkylamino groups, acyloxy groups, acyl alkyl groups, silyloxy groups, heterocyclic groups, heterocyclic-thio groups, heterocyclic-oxy groups, acyl groups, esterified carboxyl groups, and esterified thiocarboxyl groups.

On the other hand, given as additional substituents for the substituents such as amino group, amino sulfonyl group, carbamoyl group, carbamoyloxy group, carbamoyl alkyl groups, imino lower alkyl groups, and imino lower alkylamino groups, are halogen atoms, carboxyl group, thiocarboxyl group, formyl group, nitro group, cyano group, hydroxyl group, amino group, alkyl groups, alkenyl groups, aryl groups, aralkyl groups, alkylthio groups, alkenylthio groups, aralkylthio groups, arylthio groups, alkyloxy groups, alkenyloxy groups, aralkyl oxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, carbamoyl alkyl groups, imino lower alkyl groups, imino lower alkyl amino groups, acyloxy groups, acyl alkyl groups, silyloxy groups, heterocyclic groups, heterocyclic-thio groups, heterocyclic-oxy groups, acyl groups, esterified carboxyl groups, and esterified thio carboxyl groups.

In the carbapenem derivatives (I), compound (II), and compound (III) of the present invention, the following groups are given as preferred examples for the heterocyclic group represented by $R_1$, $R_5$, or $R_6$. Specifically, the heterocyclic group means a saturated or unsaturated, heteromono or hetero-polycyclic group containing at least one hetero atom, such as oxygen atom, sulfur atom, or nitrogen atom (this also applies to the heterocyclic-thio group and heterocyclic-oxy group mentioned above as the substituents). Preferred examples include 3–8 membered, preferably 5–6 membered, unsaturated hetero-monocyclic group containing 1–4 nitrogen atoms; 3–8 membered, preferably 5–6 membered, saturated hetero-monocyclic group containing 1–4 nitrogen atoms; 7–12 membered unsaturated hetero-polycyclic group containing 1–5 nitrogen atoms; 3–8 membered, preferably 5–6 membered, unsaturated hetero-monocyclic group containing 1–2 oxygen atoms and 1–3 nitrogen atoms; 3–8 membered, preferably 5–6 membered, saturated hetero-monocyclic group containing 1–2 oxygen atoms and 1–3 nitrogen atoms; 7–12 membered unsaturated hetero-polycyclic group containing 1–2 oxygen atoms and 1–3 nitrogen atoms; 3–8 membered, preferably 5–6 membered, unsaturated hetero-monocyclic group containing 1–2 sulfur atoms and 1–3 nitrogen atoms; 3–8 membered, preferably 5–6 membered, saturated hetero-monocyclic group containing 1–2 sulfur atoms and 1–3 nitrogen atoms; 7–12 membered unsaturated hetero-polycyclic group containing 1–2 sulfur atoms and 1–3 nitrogen atoms; 3–8 membered, preferably 5–6 membered, unsaturated hetero-monocyclic group containing 1–2 oxygen atoms; 3–8 membered, preferably 5–6 membered, saturated hetero-monocyclic group containing 1–2 oxygen atoms; 3–8 membered, preferably 5–6 membered, unsaturated hetero-monocyclic group containing one sulfur atom; and 3–8 membered, preferably 5–6 membered, saturated hetero-monocyclic group containing one sulfur atom.

Given as specific examples of the above-mentioned 3–8 membered unsaturated hetero-monocyclic group containing 1–4 nitrogen atoms are pyrrolyl group, pyrrolinyl group, imidazolyl group, pyrazolyl group, pyridyl group, pyrimidyl group, pyrazinyl group, pyridazinyl group, triazolyl group (for example, 4H-1,2,4-triazolyl group, 1H-1,2,3-triazolyl group, 2H-1,2,3-triazolyl group), tetrazolyl group (for example, 1H-tetrazolyl group, 2H-tetrazolyl group), dihydrotriazinyl group (for example, 4,5-dihydro-1,2,4-triazinyl group, 2,5-dihydro-1,2,4-triazinyl group), and the like; as the above-mentioned 3–8 membered saturated hetero-monocyclic group containing 1–4 nitrogen atoms, azetidinyl group, pyrrolidinyl group, imidazolidinyl group, piperidinyl group, pyrazolidinyl group, piperazinyl group, and the like; and as the above-mentioned 7–12 membered unsaturated hetero-polycyclic group containing 1–5 nitrogen atoms, indolyl group, isoindolyl group, indolizinyl group, benzimidazolyl group, quinolyl group, isoquinolyl group, indazolyl group, benzotriazolyl group, tetrazolopyridyl group, tetrazolopyridazinyl group (for example, tetrazolo[1,5-b]pyridazinyl group), dihydrotriazolopyridazinyl group, and the like.

Further, given as specific examples of the above-mentioned 3–8 membered unsaturated hetero-monocyclic group containing 1–2 oxygen atoms and 1–3 nitrogen atoms are oxazolyl group, isooxazolyl group, oxadiazolyl group (for example, 1,2,4-oxadiazolyl group, 1,3,4-oxadiazolyl group, 1,2,5-oxadiazolyl group), and the like; as the above-mentioned 3–8 membered saturated hetero-monocyclic group containing 1–2 oxygen atoms and 1–3 nitrogen atoms, morpholinyl group and the like; and as the above-mentioned 7–12 membered unsaturated hetero-polycyclic group containing 1–2 oxygen atoms and 1–3 nitrogen atoms, a benzoxazolyl group, benzoxadiazolyl group, and the like.

Specific examples of the above-mentioned 3–8 membered unsaturated hetero-monocyclic group containing 1–2 sulfur atoms and 1–3 nitrogen atoms include 1,3-thiazolyl group, 1,2-thiazolyl group, thiazolinyl group, thiadiazolyl group (for example, 1,2,4-thiadiazolyl group, 1,3,4-thiadiazolyl group, 1,2,5-thiadiazolyl group, 1,2,3-thiadiazolyl group), and the like; of the above-mentioned 3–8 membered saturated hetero-monocyclic group containing 1–2 sulfur atoms and 1–3 nitrogen atoms include thiazolidinyl group and the like; and of the above-mentioned 7–12 membered unsaturated hetero-polycyclic group containing 1–2 sulfur atoms and 1–3 nitrogen atoms include benzothiazolyl group, benzothiadiazolyl group, and the like.

Specific examples of the above-mentioned 3–8 membered unsaturated hetero-monocyclic group containing 1–2 oxygen atoms are furanyl group, pyranyl group, and the like; of the above-mentioned 3–8 membered saturated hetero-monocyclic group containing 1–2 oxygen atoms include tetrahydrofuranyl group, tetrahydropyranyl group, and the like; of the above-mentioned 3–8 membered unsaturated hetero-monocyclic group containing one sulfur atom include thienyl group and the like; and of the above-mentioned 3–8 membered saturated hetero-monocyclic group containing one sulfur atom include tetrahydrothienyl group and the like.

Beside the above-mentioned groups, heterocyclic groups possessing an N-oxide, S-oxide, or carbonyl group in the ring may be used. In addition, the heterocyclic group including a tertiary nitrogen atom may include a suitable substituent (e.g., a lower alkyl group, hydroxy lower alkyl group) to which this nitrogen atom is bonded forming a intramolecular quaternary salt, such as N-methyl pyridinium group.

These heterocyclic group may have one or more substituents. Examples of such substituents include halogen atoms such as fluorine atom, chlorine atom, and bromine atom; carboxyl group; thiocarboxyl group; formyl group; nitro group; cyano group; hydroxyl group; amino group; imino group; linear or branched lower alkyl groups such as methyl group, ethyl group, n-propyl group, isopropyl group, n-butyl group, tert-butyl group, and hexyl group; mono or polycyclic alkyl groups such as cyclopentyl group, cyclohexyl group, menthyl group, fenchyl group, and bornyl group; linear or branched lower alkenyl groups such as vinyl group, allyl group, 1-propenyl group, 2-butenyl group, 2-methyl-2-propenyl group; aryl groups having 6–10 carbon atoms such as phenyl group and naphthyl group; and aralkyl groups having 7–24 carbon atoms such as benzyl group, phenethyl group, trityl group, and benzhydryl group.

Given as further examples of the substituents are alkylthio groups, alkenylthio groups, aralkylthio groups, arylthio groups, alkyloxy groups, alkenyl oxy groups, aralkyloxy groups, and aryloxy groups, each corresponding to the above-mentioned alkyl groups, alkenyl groups, aralkyl groups, and aryl groups; alkyl sulfinyl groups and alkyl sulfonyl groups corresponding to the above-mentioned alkyl groups; aralkyl sulfinyl groups and aralkyl sulfonyl groups corresponding to the above-mentioned aralkyl groups; aryl sulfinyl groups and aryl sulfonyl groups corresponding to the above-mentioned aryl groups; amino sulfonyl group; carbamoyl group; carbamoyloxy group; carbamoyl alkyl groups; imino lower alkyl groups; imino lower alkyl amino groups; unsaturated cyclic compound groups having 5–7 carbon atoms such as cyclohexenyl group and groups containing a carbonyl group in the ring; condensed cyclic groups having 9–11 carbon atoms such as indanonyl group, tetralonyl group, and benzsuberonyl group and groups containing a carbonyl group in the ring; acyloxy groups and acyl alkyl groups corresponding to the below-mentioned acyl groups; the below-mentioned silyloxy groups; and the above-mentioned heterocyclic groups, heterocyclic-thio groups, heterocyclic-oxy groups; the below-mentioned acyl groups, esterified carboxyl groups, and esterified thiocarboxyl groups.

These substitution groups may further be substituted by one or more substituents such as, for example, the above-described substitution groups. Given as specific examples of such additional substituents for the above-mentioned substitution alkyl groups (the same applies to the above-mentioned alkylthio groups, alkyloxy groups, alkyl sulfinyl groups, and alkyl sulfonyl groups) are halogen atoms, carboxyl group, thiocarboxyl group, formyl group, nitro group, cyano group, hydroxyl group, aminogroup, alkenyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, imino group, imino lower alkyl amino groups, acyloxy groups, silyloxy groups, heterocyclic groups, heterocyclic-thio groups, heterocyclic-oxy groups, acyl groups, esterified carboxyl groups, and esterified thiocarboxyl groups.

Given as examples of such additional substituents for the above-mentioned substitution alkenyl groups are (the same applies to the alkenylthio groups, alkenyloxy groups) are halogen atoms, carboxyl group, thiocarboxyl group, formyl group, nitro group, cyano group, hydroxyl group, amino group, alkyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyl oxy group, carbamoyl alkyl groups, imino lower alkyl groups, imino lower alkyl amino groups, acyloxy groups, acyl alkyl groups, silyloxy groups, heterocyclic groups, heterocyclic-thio groups, heterocyclic-oxy groups, acyl groups, esterified carboxyl groups, and esterified thiocarboxyl groups.

Further, given as examples of such additional substituents for the above-mentioned substitution aralkyl groups (the same applies to the aralkylthio groups, aralkyloxy groups, aralkyl sulfinyl groups, and aralkyl sulfonyl groups) are halogen atoms, carboxyl group, thiocarboxyl group, formyl group, nitro group, cyano group, hydroxyl group, amino group, alkyl groups, alkenyl groups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, carbamoyl alkyl groups, imino lower alkyl groups, imino lower alkyl amino groups, acyloxy groups, acyl alkyl groups, silyloxy groups, heterocyclic groups, heterocyclic-thio groups, heterocyclic-oxy groups, acyl groups, esterified carboxyl groups, and esterified thiocarboxyl groups.

Given as examples of such additional substituents for the above-mentioned substitution aryl groups (the same applies to the arylthio groups, aryloxy groups, aryl sulfinyl groups, and aryl sulfonyl groups) are halogen atoms, carboxyl group, thiocarboxyl group, formyl group, nitro group, cyano group, hydroxylgroup, aminogroup, alkylgroups, alkenylgroups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, carbamoyl alkyl groups, imino lower alkyl groups, imino lower alkylamino groups, acyloxy groups, acyl alkyl groups, silyloxy groups, heterocyclic groups, heterocyclic-thio groups, heterocyclic-oxy groups, acyl groups, esterified carboxyl groups, and esterified thiocarboxyl groups.

On the other hand, given as additional substituents for the substituents such as amino group, imino group, amino sulfonyl group, carbamoyl group, carbamoyloxy group, carbamoyl alkyl groups, imino lower alkyl groups, imino lower alkylamino groups, unsaturated cyclic compound groups, and condensed cyclic groups, are halogen atoms, carboxyl group, thiocarboxyl group, formyl group, nitro group, cyano group, hydroxyl group, aminogroup, alkylgroups, alkenylgroups, aryl groups, aralkyl groups, alkylthio groups, alkenylthio groups, aralkylthio groups, arylthio groups, alkyloxy groups, alkenyloxy groups, aralkyloxy groups, aryloxy groups, alkyl sulfinyl groups, alkyl sulfonyl groups, aralkyl sulfinyl groups, aralkyl sulfonyl groups, aryl sulfinyl groups, aryl sulfonyl groups, amino sulfonyl group, carbamoyl group, carbamoyloxy group, carbamoyl alkyl groups, imino lower alkyl groups, imino lower alkyl amino groups, acyloxy group, acyl alkyl groups, silyloxy groups, heterocyclic groups, heterocyclic-thio groups, heterocyclic-oxy groups, acyl groups, esterified carboxyl groups, and esterified thiocarboxyl groups.

Acyl groups are given as other preferred examples of $R_5$ and $R_6$ in the compounds (II) and (III) of the present invention. Specific examples of the acyl group (the same applies to the acyloxy groups and acyl alkyl groups) include alkyl carbonyl groups, alkenyl carbonyl groups, aralkyl carbonyl groups, aryl carbonyl groups, heterocyclic carbonyl groups, and imino lower alkyl carbonyl groups, each corresponding to the aforementioned alkyl groups, alkenyl groups, aralkyl groups, aryl groups, heterocyclic groups, and imino lower alkyl groups.

As examples of the silyloxy groups mentioned above as substituents, tri-substituted silyloxy groups are given. Specific examples include trialkylsilyloxy group, aryl (alkyl) alkoxysilyloxy group, alkoxydiarylsilyloxy group, triarylsilyloxy group, alkyldiarylsilyloxy group, aryldialkylsilyloxy group, triaralkylsilyloxy group, and the like.

Given as specific examples of the silyloxy groups are trimethylsilyloxy group, triethylsilyloxy group, tri-isopropylsilyloxy group, dimethylhexylsilyloxy group, tert-butyldimethylsilyloxy group, methyl-di-isopropylsilyloxy group, isopropyldimethylsilyloxy group, tert-butylmethoxyphenylsilyloxy group, tert-butoxydiphenylsilyloxy group, triphenylsilyloxy group, tert-butyldiphenylsilyloxy group, dimethylcumylsilyloxy group, tribenzylsilyloxy group, and-the like.

Further, given as examples of the esterified carboxyl groups and esterified thiocarboxyl groups are carboxyl groups and thiocarboxyl groups which are esterified by the above-described alkyl groups, alkylthio groups, alkyloxy groups, alkenyl groups, alkenylthio groups, alkenyloxy groups, aralkyl groups, aralkylthio groups, aralkyloxy groups, aryl groups, arylthio groups, aryloxy groups, carbamoylalkyl groups, imino lower alkyl groups, acyl alkyl groups, silyl groups (the same as the silyl groups in the above-mentioned silyloxy groups), heterocyclic groups, heterocyclic-thio groups, and heterocyclic-oxy groups.

On the other hand, as the protective group for the carboxyl group represented by $R_2$ or $R_4$, any protective groups commonly used in the technological field of β-lactam compounds, which are capable of forming an ester together with carboxyl group and being removed by hydrolysis, photolysis, oxidation, or reduction, or enzymatically or of which the ester parts can be removed in vivo forming free carboxylic acid, can be used without any specific limitations.

The following esters can be given as preferred examples of this protective group for the carboxyl group.

First, givens as examples of esters which the protective group for carboxyl group form are tri-substituted silyl esters such as trialkyl silyl ester, aryl (alkyl)alkoxyl silyl ester, alkoxyldiaryl silyl ester, triarylsilyl ester, alkyldiaryl silyl ester, aryldialkyl silyl ester, and triaralkyl silyl ester (for example, trimethylsilyl ester, triethylsilyl ester, tri-isopropyl silyl ester, dimethylhexyl silyl ester, tert-butyldimethyl silyl ester, methyl-di-isopropyl silyl ester, isopropyldimethyl silyl ester, tert-butylmethoxyphenyl silyl ester, tert-butoxydiphenyl silyl ester, triphenylsilyl ester, tert-butyldiphenyl silyl ester, dimethylcumyl silyl ester, tribenzyl silyl ester, and the like); tri-substituted silyl lower alkyl esters such as, for example, trialkyl silyl lower alkyl esters, aryl(alkyl)alkoxyl silyl lower alkyl esters, alkoxyldiaryl silyl lower alkyl esters, triaryl silyl lower alkyl esters, alkyldiaryl silyl lower alkyl esters, aryldialkyl silyl lower alkyl esters, triaralkyl silyl lower alkyl esters (for example, the lower alkyl groups (e.g., linear or branched lower alkyl groups such as methyl group, ethyl group, n-propyl group, isopropyl group, n-butyl group, tert-butyl group, and hexyl group) with the above-mentioned tri-substituted silyl groups being substituted); and the like.

Further, given as examples of the esters formed by the above-mentioned protective group for carboxyl group are aromatic heterocyclic esters; lower alkyl esters; lower alkyl esters which may be substituted by one or more groups selected from lower alkanoyloxy(lower)alkyl esters, lower alkane sulfonyl(lower)alkyl esters, mono-(or di- or tri-)halo (lower)alkyl esters, lower alkoxyl carbonyloxy (lower)alkyl esters, phthalidylidene(lower)alkyl esters, (5-lower alkyl(or aryl)-2-oxo-1,3-dioxolen-4-yl)(lower)alkyl esters, and the like; lower alkenyl esters (e.g., vinyl ester, allyl ester); and lower alkynyl esters (e.g., ethynyl ester, propynyl ester).

Among the esters which are formed by the above-mentioned protective group for carboxyl group, given as specific examples of aromatic heterocyclic esters are pyridyl ester, pyrimidinyl ester, pyrazinyl ester, and pyridazinyl ester; and as specific examples of lower alkyl esters are methyl ester, ethyl ester, n-propyl ester, isopropyl ester, n-butyl ester, isobutyl ester, tert-butyl ester, pentyl ester, and hexyl ester.

Among the lower alkyl ester which may have one or more appropriate substituents, given as specific examples of lower alkanoyloxy(lower)alkyl esters are acetoxy methyl ester, propionyloxy methyl ester, butyryloxy methyl ester, valeryloxy methyl ester, pivaloyloxy methyl ester, hexanoyloxy methyl ester, 1-(or 2-)acetoxy ethyl ester, 1-(or 2- or 3-)acetoxy propyl ester, 1-(or 2-, 3-, or 4-)acetoxy butyl ester, 1-(or 2-)propionyloxy ethyl ester, 1-(or 2- or 3-)propionyloxypropyl ester, 1-(or 2-)butyryloxy ethyl ester, 1-(or 2-)iso-butyryloxy ethyl ester, 1-(or 2-)pivaloyloxy ethyl ester, 1-(or 2-)hexanoyloxy ethyl ester, iso-butyryloxy methyl ester, 2-ethylbutyryloxy methyl ester, 3,3-dimethylbutyryloxy methyl ester, 1-(or 2-)pentanoyloxy ethyl ester and the like.

Among the lower alkyl ester which may have one or more appropriate substituents, given as specific examples of lower alkane sulfonyl(lower)alkyl esters are 2-mesylethyl ester and the like; as specific examples of mono(or di or tri)halo (lower)alkyl esters are 2-iodoethyl ester, 2,2-dichloroethyl ester, 2,2,2-trichloroethyl ester and the like; as specific examples of lower alkoxyl carbonyloxy(lower)alkyl esters are methoxycarbonyloxy methyl ester, ethoxycarbonyloxy methyl ester, propoxycarbonyloxy methyl ester, tertbutoxycarbonyloxy methyl ester, 1-(or 2-)methoxycarbonyloxy ethyl ester, 1-(or 2-)ethoxycarbonyloxy ethyl ester, 1-(or 2-)iso-propoxycarbonyloxy ethyl ester and the like; and as specific examples of (5-lower alkyl (or aryl)-2-oxo-1,3-dioxolen-4-yl)(lower)alkyl esters are (5-methyl (or phenyl)-2-oxo-1,3-dioxolen-4-yl)methyl ester, (5-ethyl-2-oxo-1,3-dioxolen-4-yl)methyl ester, (5-propyl (or phenyl)-2-oxo-1,3-dioxolen-4-yl)ethyl ester and the like.

The other esters formed by the protective group for carboxyl group include aryl lower alkyl esters which may have one or more appropriate substituents (for example, benzyl ester, 4-methoxybenzyl ester, 4-nitrobenzyl ester, 2-nitrobenzyl ester, phenethyl ester, trityl ester, benzhydryl ester, bis(methoxyphenyl)methyl ester, 3,4-dimethoxybenzyl ester, 4-hydroxy-3,5-ditert-butylbenzyl ester) and the like; aryl esters which may have one or more appropriate substituents (for example, phenyl ester, 4-chlorophenyl ester, tolyl ester, tert-butyl phenyl ester, xylyl ester, mesityl ester, cumenyl ester); and phthalidyl ester.

On the other hand, as the protected hydroxyl group which is shown by $OR_7$ in the compound (III), hydroxyl groups protected by a common protective group for hydroxyl group can be used without any specific limitations.

Given as these protected hydroxyl groups are tri-substituted silyloxy groups, such as trialkyl silyloxy group, aryl(alkyl)alkoxyl silyloxy group, alkoxyl diaryl silyloxy group, triaryl silyloxy group, alkyl diaryl silyloxy group, aryl dialkyl silyloxy group, and triaralkyl silyloxy group; lower alkoxyl groups which may have one or more appropriate substituents; lower alkanoyloxy groups which may have one or more appropriate substituents; lower alkoxyl carbonyloxy groups which may have one or more appropriate substituents; lower alkenyl oxy carbonyloxy groups which may have one or more appropriate substituents; aryl carbonyloxy groups which may have one or more appropriate substituents; aralkyloxy carbonyloxy groups which may have one or more appropriate substituents; aryloxy carbonyloxy groups which may have one or more appropriate substituents; aralkyloxy groups which may have one or more appropriate substituents; and heterocyclic-oxy groups which may have one or more appropriate substituents.

Among the above-mentioned protected hydroxyl groups, given as specific examples of trisubstituted silyloxy groups are trimethyl silyloxy group, triethyl silyloxy group, tri-isopropyl silyloxy group, dimethylhexyl silyloxy group, tert-butyldimethyl silyloxy group, methyl-di-isopropyl silyloxy group, isopropyldimethyl silyloxy group, tert-butylmethoxyphenyl silyloxy group, tert-butoxydiphenyl silyloxy group, triphenyl silyloxy group, tert-butyldiphenyl silyloxy group, dimethylcumyl silyloxy group, and tribenzyl silyloxy group.

Further, as specific examples of the lower alkoxyl group which may have one or more appropriate substituents methoxy methoxy group, methoxy ethoxy methoxy group, and triphenyl methoxy group are given. As specific examples of the lower alkanoyloxy group which may have one or more appropriate substituents are acetoxy group, chloroacetoxy group, methoxy acetoxy group, propionyloxy group, butyryloxy group, iso-butyryloxy group, valeryloxy group, pivaloyloxy group, hexanoyloxy group, 2-ethylbutyryloxy group, 3,3-dimethyl butyryloxy group, and pentanoyloxy group.

Given as specific examples of the lower alkoxyl carbonyloxy groups which may have one or more appropriate substituents are methoxy carbonyloxy group, ethoxy carbonyloxy group, propoxy carbonyloxy group, iso-propoxy carbonyloxy group, tert-butoxy carbonyloxy group, 2-iodoethoxy carbonyloxy group, 2,2-dichloroethoxy carbonyloxy group, and 2,2,2-trichloroethoxy carbonyloxy group.

As specific examples of the lower alkenyloxy carbonyloxy groups which may have one or more appropriate substituents are vinyloxy carbonyloxy group, allyloxy carbonyloxy group, and 2-chloroallyloxy carbonyloxy group. Benzoyloxy group and the like are given as specific examples of the aryl carbonyloxy groups which may have one or more appropriate substituents.

Moreover, as specific examples of the aralkyloxy carbonyloxy groups which may have one or more appropriate substituents are benzyloxy carbonyloxy group, p-nitrobenzyloxy carbonyloxy group, p-methoxybenzyloxy carbonyloxy group, phenethyloxy carbonyloxy group, trityloxy carbonyloxy group, benzhydryloxy carbonyloxy group, bis(methoxyphenyl)methyloxy carbonyloxy group, 3,4-dimethoxybenzyloxy carbonyloxy group, and 4-hydroxy-3,5-di-tert-butylbenzyloxy carbonyloxy group. As specific examples of the aryloxy carbonyloxy group which may have one or more appropriate substituents are phenyloxy carbonyloxy group, 4-chlorophenyloxy carbonyloxy group, tolyloxy carbonyloxy group, tert-butylphenyloxy carbonyloxy group, xylyloxy carbonyloxy group, mesityloxy carbonyloxy group, and cumenyl oxy carbonyloxy group.

Finally, as specific examples of the aralkyloxy group which may have one or more appropriate substituents are benzyloxy group, p-nitrobenzyloxy group, p-methoxybenzyloxy group, p-tert-butylbenzyloxy group, 3,4-dimethyl benzyloxy group, 2,4-dimethoxybenzyloxygroup, benzhydryloxy group, and trityloxy group; and tetrahydropyranyloxy group and the like are given as specific examples of the heterocyclic-oxy groups which may have one or more appropriate substituents.

The compounds having the groups enumerated below for $R_1$, which is the substituent on the position 2 of the carbapenem ring in the formula (I), are given as the carbapenem derivatives (I) or a pharmaceutically acceptable salt thereof of the present invention: hydrogen atom, methyl group, ethyl group, n-propyl group, isopropyl group, n-butyl group, isobutyl group, tert-butyl group, n-pentyl group, neopentyl group, 2-hydroxyethyl group, 3-hydroxypropyl group, 2-aminoethyl group, 2-amino-2-iminoethyl group, 3-aminopropyl group, fluoromethyl group, 2-fluoroethyl groups, 3-fluoropropyl group, 2-phenoxyethyl group, 3-phenoxypropyl group, 2-[(1-iminoethyl)amino]ethyl group, 3-[(1-iminoethyl)amino]propyl group, 2-[(1-imino-1-phenylmethyl)amino]ethyl group, 2-[N-methyl-N-(2-oxo-2-phenylethyl)amino]ethyl group, 2-(pyrrolidin-1-yl)ethyl group, 2-(piperidin-1-yl)ethyl group, 2-(piperazin-1-yl)ethyl group, 2-(pyrrol-1-yl)ethyl group, N-methylcarbamoylmethyl group, N-benzylcarbamoylmethyl group, N-phenylcarbamoylmethyl group, N-methylcarbamoylethyl group, N-benzylcarbamoylethyl group, N-phenylcarbamoylethyl group, 2-morpholino-2-oxoethyl group, [o-(N-methylcarbamoyl)phenyl]methyl group, [o-(N-benzylcarbamoyl)phenyl]methyl group, cyclopropyl group, cyclopentyl group, cyclohexyl group, 1-indanyl group, 2-indanyl group, 1-indanon-2-yl group, 1-indanon-3-yl group, 6,7-dihydro-5H-cyclopenta[b]pyridin-5-yl group, 6,7-dihydro-5H-cyclopenta[b]pyridin-6-yl group, 6,7-dihydro-5H-cyclopenta [b]pyridin-7-yl group, vinyl group, allyl group, phenyl group, p-tolyl group, p-methoxyphenyl group, 2-pyridyl group, 3-pyridyl group, 4-pyridyl group, 1-naphthyl group, 2-naphthyl group, 2-quinolyl group, 4-quinolyl group, 2-thiazolyl group, 4-phenylthiazol-2-yl group, benzothiazol-2-yl group, benzyl group, diphenylmethyl group, trityl group, (1-pyridinio) methyl group, (2-pyridyl)methyl group, (1-methyl-2-pyridinio)methyl group, (1-carbamoylmethyl-2-pyridinio) methyl group, (3-pyridyl)methyl groups, (1-methyl-3-pyridinio)methyl group, (1-carbamoylmethyl-3-pyridinio) methyl group, (4-pyridyl)methyl group, (1-methyl-4-pyridinio)methyl group, (1-carbamoylmethyl-4-pyridinio) methyl group, (2-pyrimidyl)methyl group, (imidazol-2-yl) methyl group, (1-methylimidazol-2-yl)methyl group, (1-methylimidazolium-3-yl)methyl group, (1-benzylimidazol-2-yl)methyl group, (thiazol-2-yl)methyl group, phenethyl group, 2,2-diphenylethyl group, (1-pyridinio)ethyl group, 2-(2-pyridyl)ethyl group, 2-(1-methyl-2-pyridinio)ethyl group, 2-(1-carbamoylmethyl-2-pyridinio)ethyl group, 2-(3-pyridyl)ethyl group, 2-(1-methyl-3-pyridinio)ethyl group, 2-(1-carbamoylmethyl-3-pyridinio)ethyl group, 2-(4-pyridyl)ethyl group, 2-(1-methyl-4-pyridinio)ethyl group, 2-(1-carbamoylmethyl-4-pyridinio)ethyl group, 2-(2-pyrimidyl)ethyl group, 2-(imidazol-2-yl)ethyl group, 2-(1-methylimidazolium-3-yl)ethyl group, 2-(thiazol-2-ly)ethyl group, 3-phenylpropyl group, 3,3-diphenylpropyl group, (1-pyridinio)propyl group, 3-(2-pyridyl)propyl group, 3-(1-methyl-2-pyridinio) propyl group, 3-(1-carbamoylmethyl-2-pyridinio)propyl group, 3-(3-pyridyl)propyl group, 3-(1-methyl-3-pyridinio) propyl group, 3-(1-carbamoylmethyl-3-pyridinio)propyl group, 3-(4-pyridyl)propyl group, 3-(1-methyl-4-pyridinio) propyl group, 3-(1-carbamoylmethyl-4-pyridinio)propyl group, 3-(2-pyrimidyl)propyl group, 3-(imidazol-2-yl) propyl group, 3-(1-methylimidazolium-3-yl)propyl group, 3-(thiazol-2-yl)propyl group, 1-naphthylmethyl group, 2-naphthylmethyl group, 2-(1-naphthyl)ethyl group, 2-(2-naphthyl)ethyl group, (o-hydroxymethyl)benzyl group, [o-(1-methylimidazolium-3-yl)methyl]benzyl group, (m-hydroxymethyl)benzyl group, [m-(1-methylimidazolium-3-yl)methyl]benzyl group, (p-hydroxymethyl)benzyl group, [p-(1-methylimidazolium-3-yl)methyl]benzyl group, 2-amino-2-phenylethyl group, 2-amino-3-phenylpropyl group, 2-oxo-2-phenylethyl group, 2-oxo-2-(2-pyridyl)ethyl group, 2-(1-methyl-2-pyridinio)-2-oxoethyl group, 2-oxo-2-(3-pyridyl)ethyl group, 2-(1-methyl-3-pyridinio)-2-oxoethyl group, 2-oxo-2-(4-pyridyl) ethyl group, 2-(1-methyl-4-pyridinio)-2-oxoethyl group, 2-(imidazol-2-yl)-2-oxoethyl group, 2-oxo-2-(thiazol-2-yl) ethyl group, phenyl group, 1-naphthyl group, 2-naphthyl group, 2-pyridyl group, 1-methyl-2-pyridinio group, 3-pyridyl group, 1-methyl-3-pyridinio group, 4-pyridyl group, 1-methyl-4-pyridinio group, 2-pyrimidyl group, imidazol-2-yl group, thiazol-2-yl group, 4-phenyl thiazol-2-yl group, benzothiazol-2-yl group, azetidin-3-yl group, 1-allylazetidin-3-yl group, 1-benzylazetidin-3-yl group, 1-phenylazetidin-3-yl group, 1-(1-iminoethyl)azetidin-3-yl group, 1-(2-oxo-2-phenylethyl)azetidin-3-yl group, pyrrolidin-3-yl group, 2-iminopyrrolidin-3-yl group, 2-iminopyrrolidin-4-yl group, 1-allylpyrrolidin-3-yl group, 1-benzylpyrrolidin-3-yl group, 1-phenethylpyrrolidin-3-yl group, 1-cyclopropyl pyrrolidin-3-yl group, 1-cyclopentyl pyrrolidin-3-yl group, 1-(3-phenylpropyl)pyrrolidin-3-yl group, 1-phenylpyrrolidin-3-yl group, 1-(2-pyridyl) pyrrolidin-3-yl group, 1-(1-methyl-2-pyridinio)pyrrolidin-3-yl group, 1-(3-pyridyl)pyrrolidin-3-yl group, 1-(1-methyl-3-pyridinio)pyrrolidin-3-yl group, 1-(4-pyridyl)pyrrolidin-3-yl group, 1-(1-methyl-4-pyridinio)pyrrolidin-3-yl group, 1-(2-pyrimidyl)pyrrolidin-3-yl group, 1-(thiazol-2-yl) pyrrolidin-3-yl group, 1-(o-aminophenyl)pyrrolidin-3-yl group, 1-(m-aminophenyl)pyrrolidin-3-yl group, 1-(p-aminophenyl)pyrrolidin-3-yl group, 1-(p-fluorophenyl) pyrrolidin-3-yl group, 1-(p-hydroxyphenyl)pyrrolidin-3-yl group, 1-(p-methylphenyl)pyrrolidin-3-yl group, 1-(p-methoxyphenyl)pyrrolidin-3-yl group, 1-[p-(1-iminoethyl) aminophenyl]pyrrolidin-3-yl group, 1-(2-hydroxyethyl) pyrrolidin-3-yl group, 1-(2-hydroxy-2-phenylethyl) pyrrolidin-3-yl group, 1-(2-fluoroethyl)pyrrolidin-3-yl group, 1-(2-oxo-2-phenylethyl)pyrrolidin-3-yl group, 1-[2-(o-hydroxy)phenyl-2-oxoethyl]pyrrolidin-3-yl group, 1-[2-(m-hydroxy)phenyl-2-oxoethyl]pyrrolidin-3-yl groups, 1-[2-(p-hydroxy)phenyl-2-oxoethyl]pyrrolidin-3-yl group, 1-[2-(p-fluoro)phenyl-2-oxoethyl]pyrrolidin-3-yl group, 1-[2-(p-methyl)phenyl-2-oxoethyl]pyrrolidin-3-yl group, 1-[2-(p-methoxy)phenyl2-oxoethyl]pyrrolidin-3-yl group, 1-[2-(p-amino)phenyl-2-oxoethyl]pyrrolidin-3-yl group, 1-(1-methyl-2-oxo-2-phenylethyl)pyrrolidin-3-yl group, 1-(3-oxo-3-phenylpropyl)pyrrolidin-3-yl group, 1-(2-oxo-3-phenylpropyl)pyrrolidin-3-yl group, 1-(1-indanon-2-yl) pyrrolidin-3-yl group, 1-(1-indanon-3-yl)pyrrolidin-3-yl group, 1-[(1-pyridinio)methylnpyrrolidin-3-yl group, 1-[(2-pyridyl)methyl]pyrrolidin-3-yl group, 1-[(1-methyl-2-pyridinio)methyl]pyrrolidin-3-yl group, 1-[(3-pyridyl) methyl]pyrrolidin-3-yl group, 1-[(1-methyl-3-pyridinio) methyl]pyrrolidin-3-yl group, 1-[(4-pyridyl)methyl] pyrrolidin-3-yl group, 1-[(1-methyl-4-pyridinio)methyl] pyrrolidin-3-yl group, 1-?[(imidazol-2-yl)methyl] pyrrolidin-3-yl group, 1-[(1-methylimidazolium-3-yl) methyl]pyrrolidin-3-yl group, 1-iminomethylpyrrolidin-3-yl group, 1-(1-iminoethyl)pyrrolidin-3-yl group, 1-(1-imino-2-phenylethyl)pyrrolidin-3-yl group, 1-iminopropylpyrrolidin-3-yl group, piperidin-2-yl methyl group, piperidin-3-yl group, piperidin-4-yl group, 1-allylpiperidin-4-yl group, 1-benzyl piperidin-4-yl group, 1-phenylpiperidin-4-yl group, 1-(1-iminoethyl)piperidin-4-yl group, 2-hydroxymethylpyrrolidin-4-yl group, 2-(1-pyridinio)methylpyrrolidin-4-yl group, 2-(1-methylimidazolium-3-yl)methylpyrrolidin-4-yl group, 2-hydroxymethyl-1-(1-iminoethyl)pyrrolidin-4-yl group, 2-phenoxymethylpyrrolidin-4-yl group, 2-phenylmethylpyrrolidin-4-yl group, and pyrazolidin-4-yl group.

Many carbapenem derivatives (I) of the present invention have isomers. All possible isomers, other than isomers on the configuration of (1'S,5R,6R) being the characteristic feature of the compounds according to the present invention, and mixtures thereof are included in the present invention. For example, a preferred carbapenem derivative (I) of the present invention among the compounds having a pyrrolidinyl group or a substitution pyrrolidinyl group for $R_1$ is typified by the compound having (S)-pyrrolidin-3-yl group for $R_1$.

The carbapenem derivatives (I) of the present invention can be prepared by various processes. Typical processes for the synthesis of these compounds are as follows.

Method 1

The compound of the present invention of the general formula (I) can be prepared using a β-hydroxy ester of the formula (IV) as a raw material. First, the β-hydroxy ester (IV) is converted into the compound (III) according to the reactions of Process 1 shown below. This compound (III) is then subjected to the reactions of Process 2 to exchange substituents.

(Process 1)

The compound (III) which is an intermediate for preparing the compound (I) of the present invention can be prepared from β-hydroxy ester (IV) according to the following reactions.

In order to carry out the Process 1 of this method, it is necessary to convert the compound (IV) into compound (V)

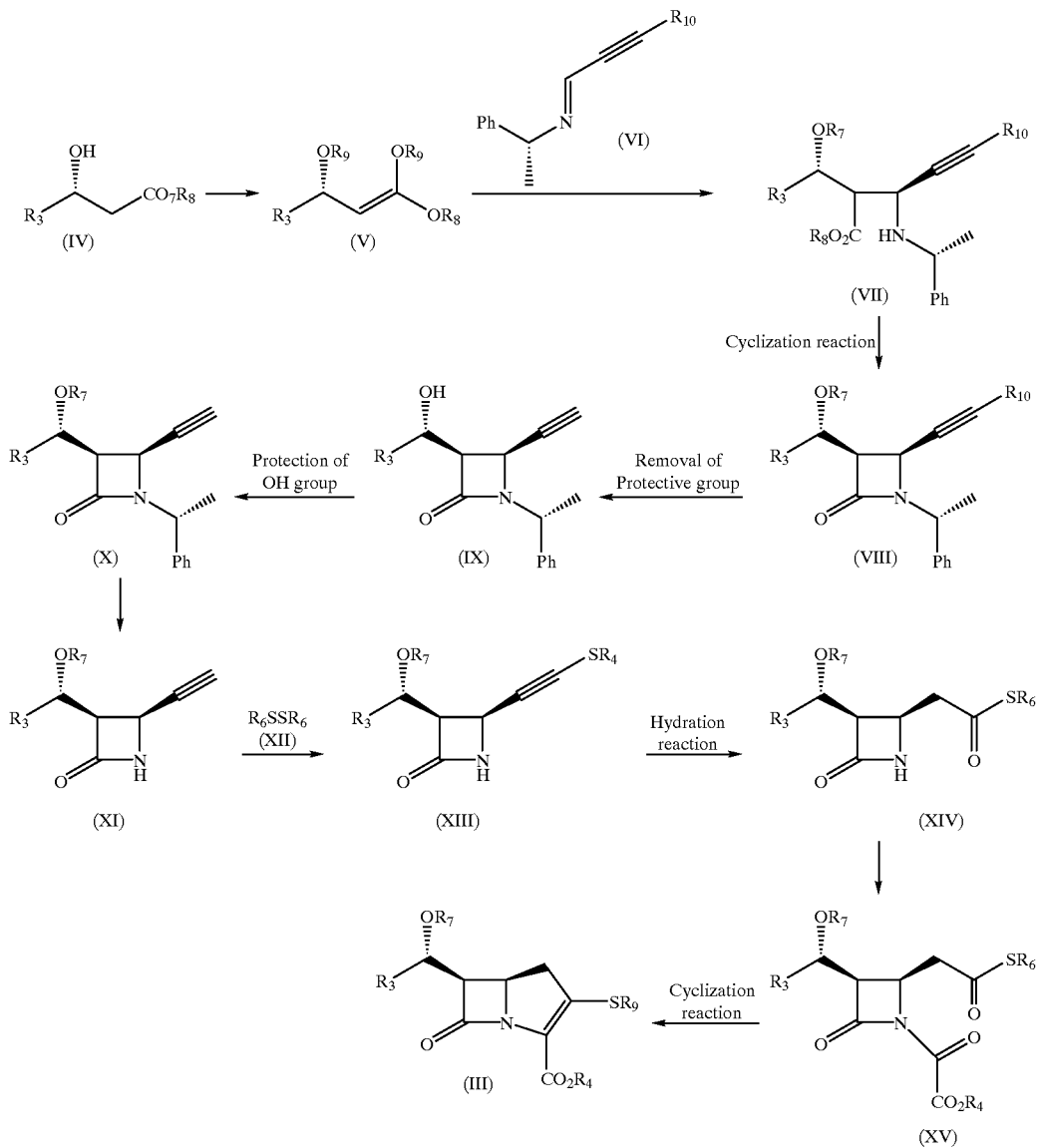

wherein $R_8$ indicates a lower alkyl group, alkenyl group, or aralkyl group; $R_9$ and $R_{10}$ represent tri-substitution silyl groups; and $R_6$ and $R_7$ have the same meanings as defined above.

As specific examples of the lower alkyl group, alkenyl group, and aralkyl group represented by $R_8$, the same groups described previously for $R_5$ and $R_6$ can be given, with particularly preferred groups being methyl group, ethyl group, allyl group, and benzyl group.

And as specific examples of the tri-substituted silyl group represented by $R_9$ and $R_{10}$, the same groups previously described as the protective group for the protected hydroxyl groups shown by $OR_7$ are given. As desirable specific examples for the group represented by $R_9$ include trimethyl silyl group, triethyl silyl group, tri-isopropyl silyl group, and tert-butyldimethyl silyl group, and particularly preferably trimethyl silyl group and triethyl silyl group. Trimethyl silyl group, triethyl silyl group, and tri-isopropyl silyl group are preferred examples of the group shown by $R_{10}$.

first of all. This reaction is carried out in a solvent such as an ether (e.g. tetrahydrofuran, diethyl ether), an aromatic hydrocarbon (e.g. toluene, benzene), or a mixture of these, at a temperature of −78 to 0° C. using a strong base such as lithium diisopropylamine, lithium hexamethyldisilazane, lithium 2,2,6,6-tetramethyl piperidine in an amount of 2–2.5 equivalent to the compound (IV), then reacting 2–3 equivalent of a tri-substituted silyl halide compound such as trimethyl silyl chloride or triethyl silyl chloride. The target compound (V) can be obtained by evaporating the solvent and filtering out insoluble matters.

If necessary, the resulting compound (V) can be purified by vacuum distillation or the like. The compound (IV) which is the starting material is a known compound and can be prepared by a conventionally known process (for example, J. Am. Chem. Soc., 109. 5856 (1987)).

The resulting compound (V) in the above reaction is reacted with an imine compound (VI) to produce the compound (VII). This reaction is carried out in a solvent such as a halogenated hydrocarbon (e.g. methylene chloride), an aromatic hydrocarbon (e.g. benzene, toluene), an ether (e.g. diethyl ether) or a mixture of these at a temperature of −78 to 0° C., preferably at −78° C., using, for one equivalent of the compound (VI), 1–2 equivalent, preferably 2 equivalent, of the compound (V), and 0.1–1 equivalent of Lewis acid, such as trialkylsilyl triflates (e.g. trimethylsilyl triflate), a boric acid ester (e.g. triphenyl borate), or a metal halide (e.g. zinc chloride), and preferably about 0.3 equivalent of trifluoromethane sulfonate. After the reaction, the reaction mixture is diluted with an organic solvent insoluble with water and washed with water, a saturated aqueous solution of sodium hydrogencarbonate, and a saturated brine in this order. Then, the solvent is evaporated to obtain the target compound (VII). If necessary, the resulting compound (VII) can be purified by column chromatography or the like.

The imine compound(VI) used in this reaction can be obtained by the condensation reaction of propargylaldehyde (J. Gen. Chem. USSR, 1996, 36, 920) and phenethyl amine in a solvent such as a halogenated hydrocarbon (e.g. methylene chloride), an aromatic hydrocarbon (e.g. benzene, toluene), a nether (e.g. diethyl ether), or a mixture of these, followed by evaporation of the solvent. The imine (VI) can also be purified by vacuum distillation or the like, if necessary.

To produce β-lactam of the formula (VIII) by cyclization of the compound (VII) obtained in this reaction, the compound (VII) is reacted with 1–1.2 equivalent of a Grignard reagent such as methyl magnesium bromide or phenyl magnesium bromide according to a method known in the art (e.g. J. Am. Chem. Soc., 1980, 102, 2060) at a temperature of −30° C. to 0° C. in a solvent such as an aromatic hydrocarbon (e.g. benzene, toluene), an ether (e.g. diethyl ether), or a mixture of these. After the reaction, the reaction mixture is diluted with an organic solvent insoluble with water and washed with saturated brine in this order. Then, the solvent is evaporated to obtain the target compound (VIII). If necessary, the compound (VIII) obtained may be purified by column chromatography or the like.

The group $R_{10}$ which is the acetylene terminal protective group in the resulting compound (VIII) is removed to produce the compound (IX). Although the reaction conditions are different according to the characteristics of the protective group to be removed, a method known in the art (for example, Japanese Patent Applications Laid-open No. 207387/1986, No. 70126/1995) is suitably selected. For example, in the case where a tri-substituted silyl group such as trimethyl silyl group is used as the protective group, such a group can easily be removed by diluting the reaction product with a solvent and causing the mixture to come contact with tetra-n-butylammoniumfluoride, triethylamine trihydrofluoride, or the like. In this instance, if a similar tri-substited silyl protective group is used as $R_9$ for a hydroxyl group, the protective group for the hydroxyl group is also removed. The reaction is carried out at a temperature of room temperature to 50° C. An ether such as tetrahydrofuran or diethyl ether, an aromatic hydrocarbon such as benzene or toluene, an ester such as ethyl acetate, a ketone such as acetone or methyl ethyl ketone, or an amide such as N,N-dimethylformamide, is preferably used as a solvent. After the reaction, the reaction mixture is diluted with an organic solvent insoluble with water and washed with a saturated aqueous solution of potassium hydrogensulfate, water, a saturated aqueous solution of sodium hydrogencarbonate, and a saturated brine in this order. Then, the solvent is evaporated to obtain the target compound (IX).

If necessary, the resulting compound (IX) can be purified by column chromatography or the like.

The hydroxyl group of the resulting compound (IX) is protected to convert this compound into the compound (X), following which the phenyl ethyl group on the position 1 of the β-lactam ring is removed.

The conditions for protection of the hydroxyl group in the compound (IX) varies according to the characteristics of the protective group used. For example, when the hydroxyl group is protected by a tert-butyldimethyl silyl group, 1–2 equivalent, preferably about 1.5 equivalent, of tert-butyldimethyl chlorosilane is reacted for one equivalent of hydroxyl group in the presence of a catalyst such as tertiary amine (e.g. triethylamine) and 4-dimethylamino pyridine according to a conventionally known method (for example, Tetrahedron Lett., 1979, 99).

The reaction is carried out at a temperature of room temperature to 50° C. An amide such as N,N-dimethylformamide, a ketone such as acetone or methyl ethyl ketone, an ether such as tetrahydrofuran or diethyl ether, or a mixture of these is preferably used as a solvent. After the reaction, the reaction mixture is diluted with an organic solvent insoluble with water and washed with a saturated aqueous solution of potassium hydrogensulfate, water, a saturated aqueous solution of sodium hydrogencarbonate, and a saturated brine in this order. Then, the solvent is evaporated to obtain the target compound (X) If necessary, the resulting compound can be purified by column chromatography or the like.

Removal of phenyl ethyl group on the position 1 of the β-lactam ring of the compound (X) is carried out by hydrogenolysis using a catalyst such as palladium, nickel, or platinum based or by Birch reduction. When the Birch reduction is applied, lithium or sodium in an amount of 1–1.5 equivalent for one equivalent of the compound (X) is reacted in ammonia or in a mixed solvent of ammonia and an ether such as tetrahydrofuran or diethyl ether at a temperature of −78° C. to −50° C. After the reaction, ammonia is evaporated, and the residue is diluted with an organic solvent insoluble with water and washed with a saturated aqueous solution of potassium hydrogensulfate, water, a saturated aqueous solution of sodium hydrogencarbonate, and a saturated brine in this order. Then, the solvent is evaporated to obtain the target compound (XI). If necessary, the resulting compound (XI) can be purified by column chromatography or the like.

To convert the terminal alkyne of the resulting compound (XI) into sulfide, thereby producing the compound (XIII), 1–1.5 equivalent of a disulfide compound of the general formula (XII) is added for one equivalent of the compound (XI) in the presence of 2–2.5 equivalent of a strong base such as n-butyl lithium, s-butyl lithium, or lithium di-isopropyl amide. The reaction is carried out at a temperature below 0° C., preferably from −78° C. to 0° C., using an ether such as tetrahydrofuran or diethyl ether as a solvent. After the reaction, the reaction mixture is diluted with an organic solvent insoluble with water and washed with a saturated aqueous solution of potassium hydrogensulfate, water, a saturated aqueous solution of sodium hydrogencarbonate, and a saturated brine in this order. Then, the solvent is evaporated to obtain the target compound (XIII). If necessary, the resulting compound (XIII) can be purified by column chromatography or the like.

Given as examples of the disulfide compound (XII) used in this sulfidation reaction are alkyl disulfide such as methyl disulfide, ethyl disulfide, propyl disulfide, n-butyl disulfide, s-butyl disulfide, t-butyl disulfide, and isopropyl disulfide;

alkenyl disulfide such as allyl disulfide; aryl disulfide such as phenyl disulfide, p-fluorophenyl disulfide, and p-nitrophenyl disulfide; aralkyl disulfide such as benzyl disulfide and p-nitrobenzyl disulfide; and heterocyclic disulfide such as 2-pyridyl disulfide and 4-pyridyl disulfide.

Conversion of the resulting compound (XIII) into a thiol ester (XIV) can be carried out by a hydration reaction according to a known method (e.g. Japanese Patent Publication 384/1991). For example, 1–5 equivalent of trifluoroacetic acid is added to the alkyne part of compound (XIII) and water is added to the reaction solvent, to convert the compound (XIII) into a thiol ester. Preferable solvents used include aromatic hydrocarbons such as toluene and benzene; ethers such as tetrahydrofuran and diethyl ether; halogenated hydrocarbons such as methylene chloride; or the mixtures of these. After the reaction, the reaction mixture is diluted with an organic solvent insoluble with water and washed with water, a saturated aqueous solution of sodium hydrogencarbonate, and a saturated brine in this order. Then, the solvent is evaporated to obtain the target compound (XIV). If necessary, the resulting compound can be purified by column chromatography or the like.

To produce the target compound (III) by cyclization of the thio ester compound (XIV), the following two-step reaction is carried out. Specifically, according to a known method (for example J. Antibiotics 1989, 42, 374 or Heterocycles 1985, 23, 1929), one equivalent of an oxalylhalide with a protective group, such as p-nitrobenzyl oxalyl chloride or allyloxalyl chloride, is reacted with the thio ester (XIV) in the presence of a base such as pyridine, triethylamine, or diisopropyl ethyl amine in an amount of one equivalent or more, thereby obtaining an imide compound (XV). This reaction is carried out preferably at a temperature of −40° C. to room temperature using a solvent such as an ether (e.g. tetrahydrofuran, diethyl ether), a halogenated hydrocarbon (e.g. methylene chloride), or a mixture of two or more of these solvent.

Next, 1 to 10 equivalent, preferably 5 equivalent, of trialkyl phosphite such as trimethyl phosphite or triethyl phosphite, is reacted with this imide compound (XV) at a reaction temperature of 80 to 150° C. in the presence or absence of a solvent, preferably an aromatic hydrocarbon such as toluene, benzene, or xylene. After the reaction, the reaction mixture is diluted with an organic solvent insoluble with water and washed with water, a saturated aqueous solution of sodium hydrogencarbonate, and a saturated brine in this order. Then, the solvent is evaporated to obtain the target compound (III). If necessary, the resulting compound can be purified by column chromatography or the like.

(Process 2)

The compound of the present invention of the general formula (I) can be prepared by exchanging the $R_6$ group on the position 2 of the carbapenem ring in the compound (III) obtained by the Process 1, according to the following reaction.

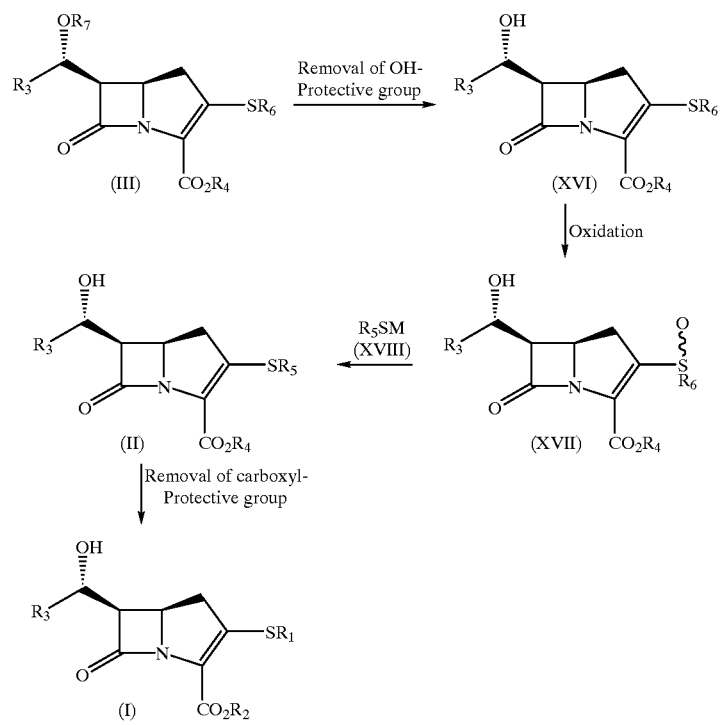

wherein M is a hydrogen atom or an alkali metal, such as sodium or potassium, $R_1$, $R_2$, $R_3$, $R_4$, $R_5$, $R_6$, and $R_7$ have the same meanings as previously defined.

Specifically, the protective group $R_7$ for the hydroxyl group of compound (III) is removed under the same conditions as the above-mentioned conditions adopted for the removal of the group $R_{10}$, to produce the compound (XVI), which is then oxidized by a conventional method (for example, Japanese Patent Application Laid-open No. 77688/1982) into a sulfoxide (XVII), followed by the reaction with a thiol compound of the general formula (XVIII), $R_5SM$ (XVIII)

wherein $R_5$ and M are the same as previously defined, or a salt thereof, to produce the compound (II), and finally removing the protective group to obtain the compound (I).

The oxidation of the compound (XVI) is carried out by reacting one equivalent of the compound (XVI) with 1.0–1.2 equivalent of a peroxy acid such as m-chloroperbenzoic acid or perphthalic acid using a halogenated hydrocarbon such as methylene chloride, an aromatic hydrocarbon such as benzene or toluene, or a saturated hydrocarbon such as hexane as a solvent at a temperature of −78° C. to 0° C. for 30 minutes to two hours. After the reaction, the reaction mixture is diluted with an organic solvent insoluble with water and washed with a saturated aqueous solution of sodium hydrogencarbonate and saturated brine in this order, and the solvent is evaporated.

The exchange reaction of the sulfoxide (XVII) obtained by the above-mentioned oxidation reaction with a thio group is carried out according to a known method (for example, Japanese Patent Application Laid-open No. 156281/1981). For instance, one equivalent of the sulfoxide (XVII) is reacted with 1–3 equivalent of thiol compound (XVIII) in the presence of 1.0–1.5 equivalent of a tertiary amine such as triethylamine or diisopropylethylamine, at a temperature of −78° C. to 0° C. for 30 minutes to 4 hours. After the reaction, the reaction mixture is diluted with an organic solvent insoluble with water and washed with a saturated aqueous solution of potassium hydrogensulfate, water, a saturated aqueous solution of sodium hydrogencarbonate, and a saturated brine in this order. Then, the solvent is evaporated to obtain the compound (II).

As specific examples of the thiol compounds of the general formula (XVIII) and the salt thereof, the following compounds and the salt thereof, for example their alkali metal salt such as sodium salt and potassium salt are given. Methane thiol, ethane thiol, n-propyl mercaptan, isopropyl mercaptan, n-butyl mercaptan, isobutyl mercaptan, tert-butyl mercaptan, n-pentyl mercaptan, neopentyl mercaptan, 2-hydroxyethyl mercaptan, 3-hydroxypropyl mercaptan, 1-mercapto-2-(N-p-nitrobenzyloxycarbonylamino)ethane, 1-mercapto-3-(N-p-nitrobenzyloxycarbonylamino)propane, 2-fluoro-1-mercaptoethane, 3-fluoro-1-mercaptopropane, 1-mercapto-2-phenoxyethane, 1-mercapto-3-phenoxypropane, 1-mercapto-2-[N-methyl-N-(2-oxo-2-phenylethyl)amino]ethane, 1-(2-mercaptoethyl)pyrrolidine, 1-(2-mercaptoethyl)piperidine, 1-(2-mercaptoethyl)pyrrole, 4-(2-mercaptoethyl)-1-(p-nitrobenzyloxycarbonyl)piperazine, cyclopropanethiol, cyclopentanethiol, cyclohexanethiol, 1-mercaptoindan, 2-mercaptoindan, 2-mercapto-1-indanone, 3-mercapto-1-indanone, 6,7-dihydro-5-mercapto-5H-cyclopenta[b]pyridine, 6,7-dihydro-6-mercapto-5H-cyclopenta[b]pyridine, 6,7-dihydro-7-mercapto-5H-cyclopenta[b]pyridine, allyl mercaptan, thiophenol, p-thiocresol, p-methoxybenzenethiol, 2-mercaptopyridine, 3-mercaptopyridine, 4-mercaptopyridine, 1-naphthalenethiol, 2-naphthalenethiol, 2-quinolinethiol, 4-quinolinethiol, 2-mercaptothiazole, 2-mercapto-4-phenylthiazole, 2-mercaptobenzothiazole, benzyl mercaptan, diphenylmethyl mercaptan, trityl mercaptan, (2-pyridyl)methyl mercaptan, (3-pyridyl)methyl mercaptan, (4-pyridyl)methyl mercaptan, (2-pyrimidyl)methyl mercaptan, (imidazol-2-yl)methyl mercaptan, (1-methyl-imidazol-2-yl)methyl mercaptan, (1-benzyl-imidazol-2-yl) methyl mercaptan, (thiazol-2-yl)methyl mercaptan, 2-phenylethanethiol, 2,2-diphenylethanethiol, 2-(2-mercaptoethyl)pyridine, 3-(2-mercaptoethyl)pyridine, 4-(2-mercaptoethyl)pyridine, 2-(2-mercaptoethyl)pyrimidine, 2-(2-mercaptoethyl)imidazole, 1-mercapto-3-phenylpropane, 1-mercapto-3,3-diphenylpropane, 2-(3-mercaptopropyl)pyridine, 3-(3-mercaptopropyl)pyridine, 4-(3-mercaptopropyl)pyridine, 2-(3-mercaptopropyl)pyrimidine, 2-(3-mercaptopropyl)imidazole, 2-(3-mercaptopropyl)thiazole, 1-naphthylmethanethiol, 2-naphthylmethanethiol, 2-(1-naphthyl)ethanethiol, 2-(2-naphthyl)ethanethiol, 2-(p-nitrobenzyloxycarbonyl)amino-2-phenylethanethiol, 2-(p-nitrobenzyloxycarbonyl)amino-3-phenylpropanethiol, 1-mercapto-2-oxo-2-phenylethane, 1-mercapto-2-oxo-2-(2-pyridyl)ethane, 1-mercapto-2-oxo-2-(3-pyridyl)ethane, 1-mercapto-2-oxo-2-(4-pyridyl)ethane, 1-mercapto-2-oxo-2-(imidazol-2-yl)ethane, 1-mercapto-2-oxo-2-(thiazol-2-yl)ethane, 3-mercapto-1-(p-nitrobenzyloxycarbonyl)azetidine, 1-allyloxycarbonyl-3-mercaptoazetidine, 1-benzyl-3-mercaptoazetidine, 3-mercapto-1-phenylazetidine, 3-mercapto-1-(2-oxo-2-phenylethyl)azetidine, 3-mercapto-1-(p-nitrobenzyloxycarbonyl)pyrrolidine, 1-allyloxycarbonyl-3-mercaptopyrrolidine, 1-benzyl-3-mercaptopyrrolidine, 3-mercapto-1-phenethylpyrrolidine, 1-cyclopropyl-3-mercaptopyrrolidine, 1-cyclopentyl-3-mercaptopyrrolidine, 3-mercapto-1-(3-phenylpropyl)pyrrolidine, 3-mercapto-1-phenylpyrrolidine, 3-mercapto-1-(2-pyridyl)pyrrolidine, 3-mercapto-1-(3-pyridyl)pyrrolidine, 3-mercapto-1-(4-pyridyl)pyrrolidine, 3-mercapto-1-(2-pyrimidyl)pyrrolidine, 1-(imidazol-2-yl)-3-mercaptopyrrolidine, 3-mercapto-1-(thiazol-2-yl)pyrrolidine, 3-mercapto-1-[4-(p-nitrobenzyloxycarbonyl)aminophenyl]pyrrolidine, 1-(2-hydroxyethyl)-3-mercaptopyrrolidine, 1-(2-hydroxy-2-phenylethyl)-3-mercaptopyrrolidine, 1-(2-fluoroethyl)-3-mercaptopyrrolidine, 3-mercapto-1-(2-oxo-2-phenylethyl) pyrrolidine, 3-mercapto-1-[2-(2-p-nitrobenzyloxy)phenyl-2-oxoethyl]pyrrolidine, 3-mercapto-1-[2-oxo-2-(3-p-nitrobenzyloxy)phenylethyl]pyrrolidine, 3-mercapto-1-[2-(4-p-nitrobenzyloxy)phenyl-2-oxoethyl]pyrrolidine, 1-[2-(p-fluoro)phenyl-2-oxoethyl]-3-mercaptopyrrolidine, 3-mercapto-1-[2-(p-methyl)phenyl-2-oxoethyl]pyrrolidine, 3-mercapto-1-[2-(p-methoxy)phenyl-2-oxoethyl]pyrrolidine, 3-mercapto-1-(1-methyl-2-oxo-2-phenylethyl)pyrrolidine, 3-mercapto-1-(3-oxo-3-phenylpropyl)pyrrolidine, 3-mercapto-1-(2-oxo-3-phenylpropyl)pyrrolidine, 1-(1-indanon-2-yl)-3-mercaptopyrrolidine, 1-(1-indanon-3-yl)-3-mercaptopyrrolidine, 3-mercapto-1-[(2-pyridyl)methyl]pyrrolidine, 3-mercapto-1-[(3-pyridyl)methyl]pyrrolidine, 3-mercapto-1-[(4-pyridyl)methyl]pyrrolidine, 2-mercaptomethyl-1-(p-nitrobenzyloxycarbonyl)piperidine, 3-mercapto-1-(p-nitrobenzyloxycarbonyl)piperidine, 4-mercapto-1-(p-nitrobenzyloxycarbonyl)piperidine, 1-allyloxycarbonyl-4-mercaptopiperidine, 1-benzyl-3-mercaptopiperidine, 3-mercapto-1-phenylpiperidine, 5-hydroxymethyl-3-mercapto-1-(p-nitrobenzyloxycarbonyl)pyrrolidine, 3-mercapto-1-(p-nitro benzyloxycarbonyl)-5-phenoxymethylpyrrolidine, 3-mercapto-1-(p-nitrobenzyloxycarbonyl)-5-phenylmethylpyrrolidine, and 4-mercapto-(1,2-di-p-nitrobenzyloxycarbonyl)pyrazolidine.

Removing the protective group $R_4$ for the carboxyl group in the resulting compound (II) can be performed if desired, the conditions differ according to the characteristics of the protective group to be removed, and can be suitably selected from the conditions known in the art (for example, Japanese Patent Applications Laid-open No. 207387/1986, No. 321952/1994). In the case of an aralkyl group such as p-nitrobenzyl group, the protective group can be removed by a catalytic hydrogenation reaction using hydrogen in the presence of a palladium-carbon catalyst.

The substituent at position 2 can also be converted at the same time, using the same means as that used for removing the protective group $R_4$ for the carboxyl group in the compound (II). The conversion which can be performed in this instance includes reduction of a double bond or triple bond, removal of protective groups for amino group, and removal of protective groups for carboxyl group.

The target compound (I) can be obtained by removing the protective group of carboxyl group in the compound (II) in this manner. If necessary, the resulting compound (I) can be purified by chromatography such as liquid chromatography or by recrystallization. In addition, isomers can be separated by chromatography such as column chromatography or by recrystallization, if necessary.

Method 2

The compound shown by the general formula (I) can also be prepared by exchanging the $R_6$ group at the position 2 of the compound (III) according to the following reactions.

of an alkali metal, such as sodium or potassium, being particularly preferred.

General antimicrobial activity and antimicrobial activity (MIC) against various methicillin resistant microorganisms (methicillin-resistant *Staphylococcus aureus*; MRSA) belonging to *Staphylococcus aureus* were investigated on the compound (I) of the present invention prepared according to the method described above. The results are shown in Table 1, wherein the tested compounds are given the same numbers as the numbers of the Examples described hereinafter. *Staphylococcus aureus* (209P JC-1) and *Escherichia coli* (NIHJ JC-2), MRSA (high resistant) were used as the microorganisms for the general antimicrobial activity.

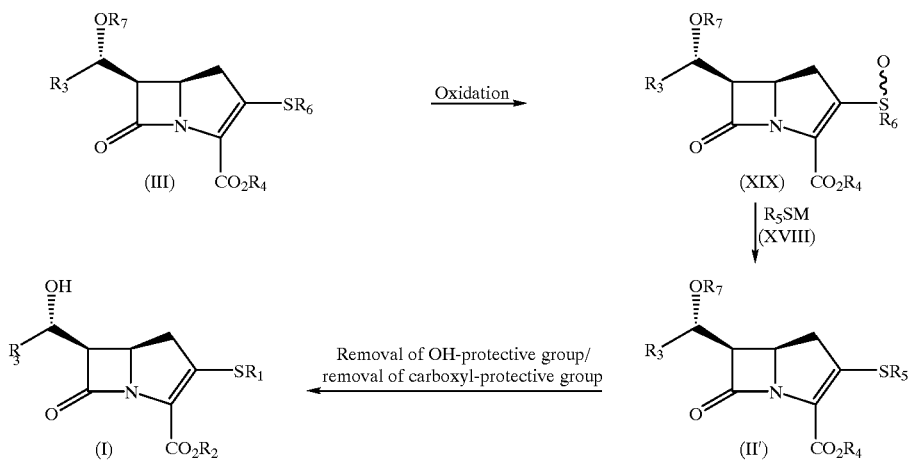

wherein $R_1$, $R_2$, $R_3$, $R_4$, $R_5$, $R_6$, $R_7$, and M have the same meanings at previously defined.

First, the compound (III) obtained by the Process 1 of the foregoing Method 1 is oxidized by the same method as the above-described method for manufacturing the compound (XVII) from the compound (XVI), to obtain a sulfoxide compound (XIX).

Next, a thiol compound or its salt (XVIII) is reacted with the sulfoxide compound (XIX) according to the method previously described in the Process 2 of the Method 1, to produce a compound (II').

In addition, if necessary, the protective groups of the hydroxyl group and/or carboxyl group in the compound (II') are removed by the above-described method to obtain the target compound (I).

Each process in this Method 2 is the same as the Processes 1 and 2 for the Method 1, and can thus be carried out according to the condition described above.

As mentioned in the description of Method 1, the substituent at the position 2 can also be converted at the same time when the protective group $R_4$ of the carboxyl group in the compound (II') is removed, the resulting compound (I) can be purified, and the isomers can be separated from the mixture.

The compound (I) of the present invention thus obtained can be acquired in the form of a pharmaceutically acceptable salt, as required. Included in such a salt are a salt of an inorganic metal such as an alkali metal (e.g. lithium, sodium, potassium) and an alkaline earth metal (e.g. calcium, magnesium), a salt of a basic amino acid such as lysine, and a salt of an organic amine such as ammonium salt, with a salt

TABLE 1

| | Tested microorganism ($10^6$ CFU/ml) | | | |
|---|---|---|---|---|
| Test Compound | MRSA 31 High resistant (IPM resistant) | MRSA 33 High resistant (IPM resistant) | S-aureus 209P JC-1 | E-coli NIHJ JC-2 |
| Example 10 Example 13 | 12.5. | 12.5 | 0.2 | 50 |
| NH compound | 6.25 | 6.25 | 0.1 | 0.1 |
| N-Allyl compound | 6.25 | 6.25 | 0.05 | 0.2 |
| Example 14 Example 25 | 6.25 | 6.25 | 0.05 | 0.2 |
| NH compound | 12.5 | 12.5 | 0.1 | 0.1 |
| N-Allyl compound | 12.5 | 12.5 | 0.1 | 0.1 |
| Example 28 | 50 | 50 | 0.39 | 0.1 |
| Example 30 | 12.5 | 12.5 | 0.05 | 0.1 |
| Example 35 | 12.5 | 12.5 | 0.39 | 12.5 |

(Unit for the numbers in the Table is μg/ml)

As clear from the results shown in the above Table, the compounds (I) of the present invention not only possess a wide antimicrobial activity, but also exhibit a strong antimicrobial activity against MRSA.

Because the compound (I) of the present invention exhibits superior antimicrobial activity against general pathogenic fungi and MRSA as mentioned above and exhibits no serious in vivo toxicity similar to other common carbapenem derivatives, the compound can be utilized widely as an antimicrobial agent for oral administration, parenteral administration, and external application.

In particular, because the compound (I) exhibits excellent activity against MRSA for which conventionally there have been no effective antibiotics, the compound is extremely valuable as an anti-MRSA agent.

Although a dose of the compound (I) of the present invention varies according to the purpose of administration and the age, weight, and condition of the subjects to whom the compound (I) is administered, a daily per-oral dose for an adult is typically 50 mg to 5 g, and preferably 100 mg to 4 g, which should desirably be administered in division several times a day. Generally, the administration should be in the form of a dosing unit containing an appropriate amount of the active ingredient and pharmaceutically acceptable vehicles or diluents.

Tablets or capsules can be used for oral administration. In addition to the active ingredient, these may comprise diluents such as lactose, glucose, sucrose, mannitol, sorbitol, and cellulose, and lubricants such as talc, stearic acid, or a salt of stearic acid. In addition, tablets may further contain a binding agent such as magnesium silicate or starch.

An isotonic aqueous solution or a suspension is suitable for parenteral administration such as intravenous administration, intrarterial administration, intramuscular administration, and subcutaneous administration. In addition, the compound (I) of the present invention is used not only as a medicine for human beings but also as an antimicrobial agent for animals.

The compound (I) possessing a specific substituent and a specific configuration structure exhibits a strong antimicrobial activity, particularly against MRSA, as can be seen from the results of the above test results. The compound is thus useful not only as a general antimicrobial agent, but also as an antimicrobial agent against MRSA for which conventionally there have been no effective antibiotics.

Other features of the invention will become apparent in the course of the following description of the exemplary embodiments which are given for illustration of the invention and are not intended to be limiting thereof.

EXAMPLES

Example 1

Methyl(2R,3S)-2-[(S)-1-(triethylsilyloxy)propyl]-3-[(R)-1-phenylethyl]amino-5-trimethylsilyl-4-yne carboxylate

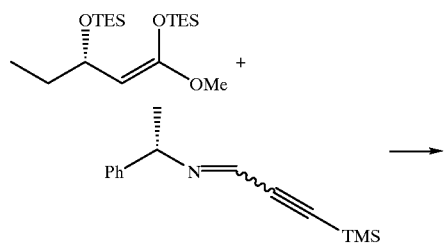

-continued

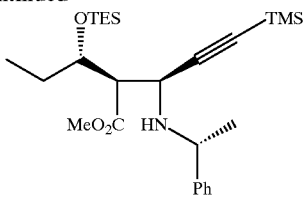

Trimethylsilyltrifluoromethane sulfonate (0.7 ml, 3.62 mmol) was added dropwise to a solution of an imine (synthesized from (S)-1-phenylethylamine and trimethylsilylpropargyl aldehyde) (8.7 g, 38.06 mmol) and (Z)-1-triethylsilyloxy-1-methoxy-3-(S)-triethylsilyloxy-1-pentene (27.4 g, 76.11 mmol) in methylene chloride (300 ml) at −78° C. in an argon atmosphere. After the addition, the temperature was raised to −30° C. in one hour and then returned to −78° C. again. Trimethylsilyltrifluoromethane sulfonate (0.7 ml, 3.62 mmol) was added dropwise to the mixture. After the addition, the temperature was allowed to rise to 0° C. in one hour and then returned to −78° C. again, whereupon trimethylsilyltrifluoromethane sulfonate (0.8 ml, 4.14 mmol) was again added dropwise. The mixture was allowed to stand while the temperature was permitted to rise to room temperature, at which temperature the mixture was stirred overnight. After the addition of saturated aqueous solution of sodium hydrogencarbonate, extraction with ethyl acetate was carried out. The organic layer was washed with saturated brine and dried over anhydrous sodium sulfate. The solvent was removed by evaporation under reduced pressure and the residue was purified by silica gel chromatography (hexane/ether=20/1) to obtain 7.93 g (yield 44%) of the title compound as a colorless oily substance.

IR(neat)cm$^{-1}$: 2960, 1742, 1250, 843

$^1$H-NMR(CDCl$_3$): δ 0.15(9H, s, Si(C$\underline{H}_3$)$_3$), 0.59(6H, q, J=7.9 Hz, Si(C$\underline{H}_2$CH$_3$)$_3$), 0.85–0.96(12H, m, C$\underline{H}_3$CH$_2$CHOSi, Si(CH$_2$C$\underline{H}_3$)$_3$), 1.30(3H, d, J=6.6 Hz, PhCHC$\underline{H}_3$), 1.46–1.68(2H, m, CH$_3$C$\underline{H}_2$CHOSi), 2.87(1H, dd, J=5.2and8.6 Hz, C$\underline{H}$CO$_2$Me), 3.66(3H, s, CO$_2$C$\underline{H}_3$), 3.88(1H, d, J=5.3 Hz, C$\underline{H}$NH), 4.01–4.10(1H, m), 4.11–4.19 (1H, m), 7.20–7.38(5H, m, Ar)

Example 2

(3R, 4S)-3-[(S)-1-(Triethylsilyloxy)propyl]-1-[(R)-1-phenylethyl]-4-[2-(trimethylsilyl)ethynyl]-2-azetidinone

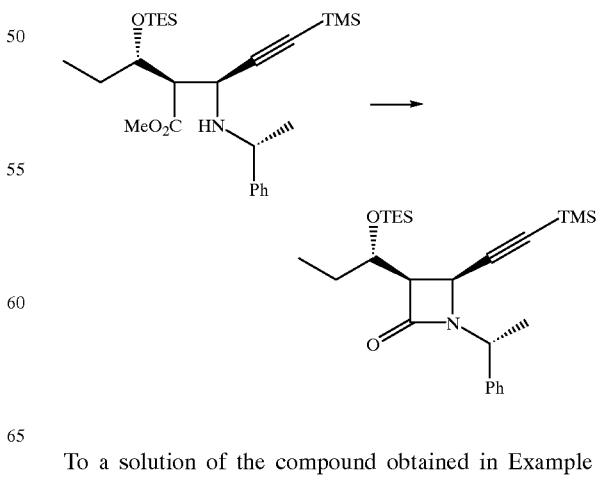

To a solution of the compound obtained in Example 1 (7.93 g, 16.69 mmol) in ether (100 ml) was added dropwise phenyl magnesium bromide (0.634 M ether solution) (29 ml, 18.36 mmol) at −10° C. in an argon atmosphere. After stirring for 10 minutes at this temperature, a saturated aqueous solution of ammonium chloride was added and the mixture was extracted with ethyl acetate. The organic layer was washed with saturated brine and dried over anhydrous sodium sulfate. The solvent was removed by evaporation under reduced pressure and the residue was purified by silica gel chromatography (hexane/ethyl acetate=20/1) to obtain 3.67 g (yield 50%) of the title compound as a colorless oily substance.

IR(neat)cm$^{-1}$: 2960, 2877, 1754, 1250, 841

$^{1}$H-NMR(CDCl$_3$): δ 0.18(9H, s, Si(CH$_3$)$_3$), 0.63(6H, q, J=7.9 Hz, Si(CH$_2$CH$_3$)$_3$), 0.85–0.98(12H, m, CH$_3$CH$_2$CHOSi, Si(CH$_2$CH$_3$)$_3$), 1.69(3H, d, J=7.2 Hz, PhCHCH$_3$), 1.71–1.83(2H, m, CH$_3$CH$_2$CHOSi), 3.27(1H, dd, J=5.2 and 6.5 Hz, C$_3$—H), 4.04(1H, d, J=5.2 Hz, C$_4$—H), 4.15–4.23(1H, m, CH$_3$CH$_2$CHOSi), 5.04(1H, q, J=7.2 Hz, PhCHCH$_3$), 7.26–7.38(5H, m, Ar)

Example 3

(3R,4S)-3-[(S)-1-hydroxypropyl]-1-[(R)-1-phenylethyl]-4-ethynyl-2-azetidinone

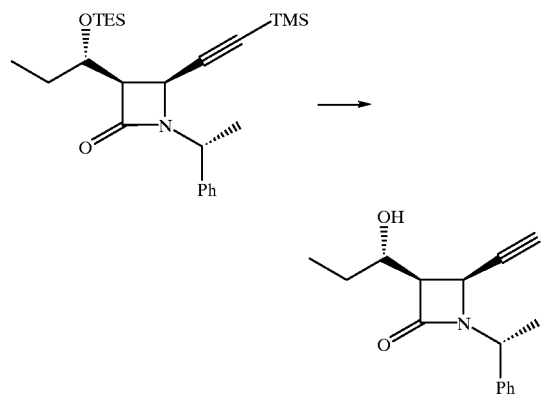

Acetic acid (1.42 ml, 24.85 mmol) and tetrabutylammonium fluoride (1M tetrahydrofuran solution)(22.4 ml, 22.37 mmol) were added dropwise to a solution of the compound prepared in Example 2 (3.67 g, 8.28 mmol) in tetrahydrofuran (42 ml) at room temperature in an argon atmosphere. After stirring for 20 hours at this temperature, a saturated aqueous solution of ammonium chloride was added and the mixture was extracted with ethyl acetate. The organic layer was washed with saturated brine and dried over anhydrous sodium sulfate. The solvent was removed by evaporation under reduced pressure and the residue was purified by silica gel chromatography (hexane/ethyl acetate=3/1) to obtain 1.61 g (yield 76%) of the title compound as a colorless oily substance.

IR(neat)cm$^{-1}$: 3452, 3284, 2972, 1740, 1383

$^{1}$H-NMR(CDCl$_3$): δ 1.04(3H, t, J=7.4 Hz, CH$_3$CH$_2$CHOH), 1.46–1.68(1H, m, CH$_3$CH(H)CHOH), 1.70 (3H, d, J=7.2 Hz, PhCHCH$_3$), 1.87–2.03(1H, m, CH$_3$CH(H)CHOH), 2.00–2.35(1H, brs, OH), 2.58 (1H, d, J=2.0 Hz, acetylene proton), 3.23(1H, dd, J=5.3 and 9.9 Hz, C$_3$—H), 4.05(1H,dd, J=2.0 and 5.3 Hz C$_4$—H), 4.10(1H, dd, J=3.3 and 9.2 Hzq, CH$_3$CH$_2$CHOH), 5.06(1H, q, J=7.2 Hz, PhCHCH$_3$), 7.26–7.41(5H, m, Ar)

Example 4

(3R,4S)-3-[(S)-1-(tert-butyldimethylsilyloxy) propyl]-1-[(R)-1-phenylethyl]-4-ethynyl-2-azetidinone

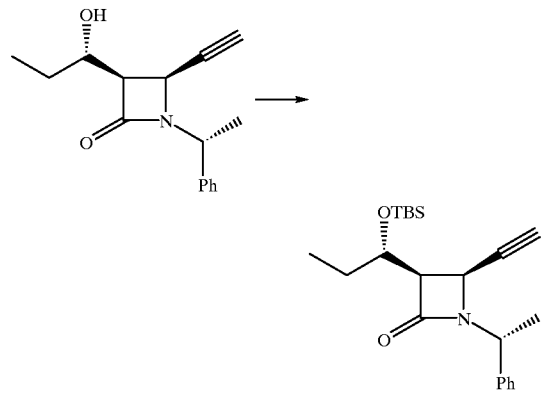

Imidazole (554 mg, 8.14 mmol) and tert-butyldimethylsilyl chloride (1.13 g, 7.52 mmol) were added to a solution of the compound (1.61 g, 6.26 mmol) prepared in Example 3 in N,N-dimethylformamide (7 ml) at room temperature in an argon atmosphere. After stirring overnight at this temperature, the mixture was diluted with ethyl acetate. The organic layer was washed with saturated aqueous solution of potassium hydrogensulfate and saturated brine in this order, and dried over anhydrous sodium sulfate. The solvent was removed by evaporation under reduced pressure and the residue was purified by silica gel chromatography (hexane/ethyl acetate=20/1) to obtain 2.157 g (yield 93%) of the title compound as a colorless oily substance.

IR(neat)cm$^{-1}$: 3240, 2933, 2856, 1754, 1377, 1252

$^{1}$H-NMR(CDCl$_3$): δ 0.08(6H, s, Si(CH$_3$)$_2$C$_4$H$_9$), 0.88 (9H, s, Si(CH$_3$)$_2$C$_4$H$_9$), 0.82–0.98(3H, m, CH$_3$CH$_2$CHOSi), 1.69(3H, d, J=7.2 Hz, PhCHCH$_3$), 1.72–1.86(2H, m, CH$_3$CH$_2$CHOSi), 2.47(1H, d, J=2.0 Hz, acetylene proton), 3.31 (1H, dd, J=5.3 and 6.6 Hz, C$_3$—H), 4.01(1H, dd, J=2.0 and 5.3 Hz, C$_4$-H), 4.18–4.29(1H, m, CH$_3$CH$_2$CHOSi), 5.08 (1H, q, J=7.2 Hz, PhCHCH$_3$), 7.25–7.40(5H, m, Ar)

Example 5

(3R,4S)-3-[(S)-1-(tert-butyldimethylsilyloxy) propyl]-4-ethynyl-2-azetidinone

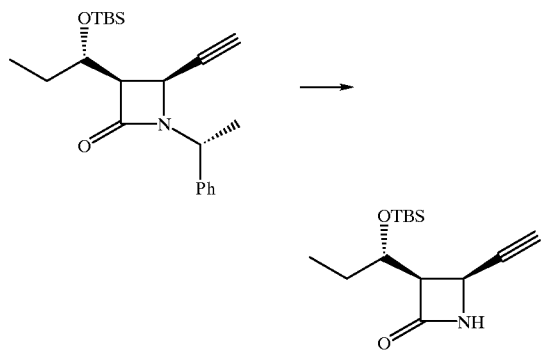

To 35 ml of ammonia were added sodium (50.4 mg, 2.19 mmol) and iron nitride nonahydrate (a catalytic amount) at −78° C. in an argon atmosphere. The mixture was stirred for 15 minutes, while the temperature was allowed to rise. Then, the temperature was returned to −78° C., followed by dropwise addition of a solution of the compound (509 mg, 1.37 mmol) prepared in Example 4 in ether (4 ml). After stirring at the same temperature for 40 minutes, sodium (189 mg, 8.20 mmol) was again added, and the mixture was stirred for a further 30 minutes at the same temperature. Next, ammonium chloride (3.5 g) and ethanol (3.5 ml) were added, followed by heating of the mixture. Ammonia was removed by evaporation, insoluble matters were removed by filtration, and the mixture was washed with ethyl acetate. The solvent was removed by evaporation under reduced pressure and the residue was purified by silica gel chromatography (hexane/ethyl acetate 4/1) to obtain 304 mg (yield 83%) of the title compound as a colorless crystals.

IR(KBr)cm$^{-1}$: 3311, 2964, 1786, 1727, 1252, 1038

$^1$H-NMR (CDCl$_3$): δ 0.10(6H, s, Si(CH$_3$)$_2$C$_4$H$_9$) 0.89(9H, s, Si(CH$_3$)$_2$C$_4$HH$_9$), 0.92–1.01 (3H, m, CH$_3$CH$_2$CHOSi), 1.72–1.88 (2H, m, CH$_3$CH$_2$CHOSi), 2.49 (1H, d, J=2.0 Hz, acetylene proton), 3.51–3.60 (1H, m, C$_3$—H), 4.22–4.33 (1H, m, CH$_3$CH$_2$CHOSi), 4.38 (1H, dd, J=2.0 and 5.3 Hz, C$_4$—H), 5.90(1H, brs, NH)

Example 6

(3R,4S)-3-((S)-1-(tert-butyldimethylsilyloxy)propyl]-4-(2-phenylthioethynyl)-2-azetidinone

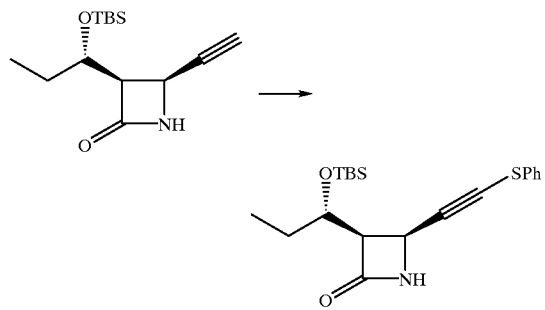

To a solution of the compound obtained in Example 5 (302 mg, 1.13 mmol) in tetrahydrofuran (4 ml) was added dropwise n-butyl lithium (1.56 M hexane solution) (1.52 ml, 2.37 mmol) at −78° C. in an argon atmosphere and the mixture was stirred for 20 minutes. Then, a solution of diphenyl disulfide (321 mg, 1.47 mmol) in tetrahydrofuran (3 ml) was slowly added dropwise at the same temperature. Thereafter, the temperature was allowed to rise to 0° C. in one hour, followed by stirring for 30 minutes at 0° C. The mixture was diluted with ethyl acetate, the organic layer was washed with saturated brine and dried over anhydrous sodium sulfate. The solvent was removed by evaporation under reduced pressure and the residue was purified by silica gel chromatography (hexane/ethyl acetate=4/1) to obtain 415 mg (yield 98%) of the title compound as a colorless oily substance.

IR(neat)cm$^{-1}$: 2930, 2856, 1760, 1252, 1112

$^1$H-NMR(CDCl$_3$): δ 0.07 and 0.08 (total 6H, each s, Si(CH$_3$)$_2$C$_4$H$_9$) 0.87(9H, s, Si(CH$_3$)$_2$C$_4$H$_9$), 0.96(3H, t, J=7.3 Hz, CH$_3$CH$_2$CHOSi), 1.74–1.89(2H, m, CH$_3$CH$_2$CHOSi), 3.57–3.65(1H, m, C$_3$—H), 4.22–4.31(1H, m, CH$_3$CH$_2$CHOSi), 4.64(1H, d, J=5.2 Hz, C$_4$—H), 6.00(1H, brs, NH),7.20–7.44(5H, m, Ar)

Example 7

(3R,4R)-3-[(S)-1-(tert-butyldimethylsilyloxy)propyl]-4-phenylthiocarbonylmethyl-2-azetidinone

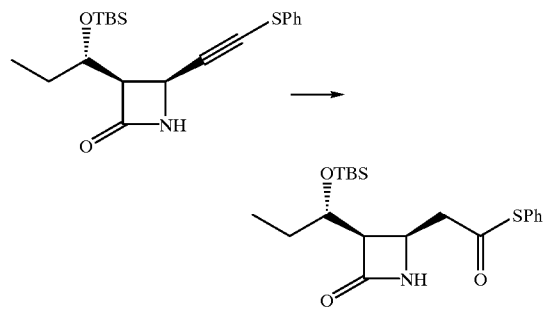

Trifluoroacetic acid (0.58 ml, 7.51 mmol) was added to a solution of the compound (564 mg, 1.50 mmol) prepared in Example 6 in methylene chloride (10 ml) at 0° C. in an argon atmosphere. The mixture was stirred for two hours at this temperature and one hour at room temperature. After the addition of sodium hydrogencarbonate (189 mg, 2.25 mmol), water (7 ml), and ethyl acetate (28 ml), the mixture was stirred at room temperature for 40 minutes and diluted with ethyl acetate. The organic layer was washed with a saturated aqueous solution of sodium hydrogencarbonate and saturated brine in this order and dried over anhydrous sodium sulfate. The solvent was removed by evaporation under reduced pressure and the residue was purified by silica gel chromatography (hexane/ethyl acetate=3/1) to obtain 432 mg (yield 73%) of the title compound as a colorless oily substance.

IR(neat)cm$^{-1}$: 2930, 1760, 1704, 1472, 1381, 1258

$^1$H-NMR(CDCl$_3$): δ 0.15 and 0.17(total 6H, each s, Si(CH$_3$)$_2$C$_4$H$_9$), 0.86–0.98(3H, m, CH$_3$CH$_2$CHOSi), 0.97(9H, s, Si(CH$_3$)$_2$C$_4$H$_9$), 1.55–1.67(1H, m, CH$_3$CH(H)CHOSi), 1.69–1.82(1H, m, CH$_3$CH(H)CHOSi), 3.26(1H, dd, J=2.9 and 16.7 Hz, CH(H)COS), 3.41–3.46(1H, m, C$_3$—H), 3.52 (1H, dd, J=10.6 and 16.7 Hz, CH(H)COS), 4.10–4.18(2H, m, CH$_3$CH$_2$CHOSi and C$_4$—H), 6.04(1H, brs, NH), 7.39–7.47(5H, m, Ar)

Example 8

Allyl(5R,6R)-2-phenylthio-6-[(S)-1-(tert-butyldimethylsilyloxy)propyl]carbapenem-3-carboxylate

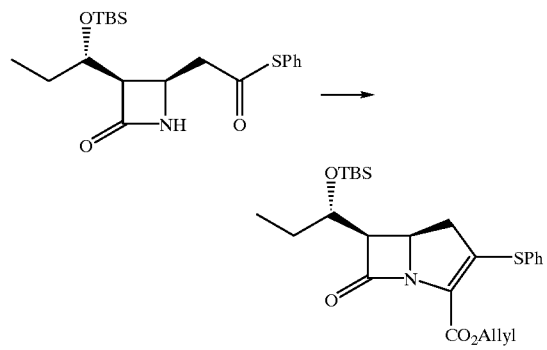

Triethylamine (0.31 ml, 2.20 mmol) and allyl oxalyl chloride (0.264 ml,2.20 mmol) were added to a solution of the compound (432 mg, 1.10 mmol) obtained in Example 7 in methylene chloride (8 ml) at −30° C. in an argon atmosphere. After stirring at this temperature for 20 minutes, the mixture was diluted with ethyl acetate. The organic layer was washed with a saturated aqueous solution of sodium hydrogencarbonate and saturated brine in this order and dried over anhydrous sodium sulfate. The solvent was removed by evaporation under reduced pressure to obtain an imide compound. Then, triethyl phosphite (1.13 ml, 6.59 mmol) was added to a xylene (1.13 ml) solution of the imide compound. After stirring for three hours at 80° C., xylene (50 ml) was added and the mixture was heated for 30 minutes while refluxing. The mixture was again diluted with ethyl acetate, the organic layer was washed with a saturated aqueous solution of potassium hydrogencarbonate, a saturated aqueous solution of sodium hydrogencarbonate, and saturated brine in this order and dried over anhydrous sodium sulfate. The solvent was removed by evaporation under reduced pressure and the residue was purified by silica gel chromatography (hexane/ethyl acetate=6/1) to obtain 277 mg (yield 53%) of the title compound as a colorless oily substance.

IR(neat)cm$^{-1}$: 2930, 1780, 1700, 1560, 1279, 1200

$^1$H-NMR(CDCl$_3$): δ 0.03 and 0.07(total 6H, each s, Si(CH$_3$)$_2$C$_4$H$_9$), 0.80–0.96(3H, m, CH$_3$CH$_2$CHOSi), 0.84(9H, s, Si(CH$_3$)$_2$C$_4$H$_9$), 1.48–1.59(1H, m, CH$_3$CH(H)CHOSi), 1.61–1.73(1H, m, CH$_3$CH(H)CHOSi), 2.42(1H, dd, J=9.8 and 18.1 Hz, C$_1$—H(H)), 3.39(1H, dd, J=9.2 and 18.1 Hz, C$_1$—H(H)), 3.62–3.68(1H, m, C$_6$—H), 4.06–4.17(2H, m, CH$_3$CH$_2$CHOSi and C$_5$—H), 4.75–4.82(1H, m, CO$_2$CH(H)), 4.75–4.92(1H, m, CO$_2$H(H)), 5.25–5.31(1H, m, CH=CH(H)), 5.46–5.55(1H, m, CH=CH(H)), 5.95–6.10 (1H, m, CH$_2$CH=CH$_2$), 7.36–7.47(3H, m, Ar), 7.55–7.62 (2H, m, Ar)

Example 9

Allyl (5R,6R)-2-phenylthio-6-[(S)-1-hydroxypropyl] carbapenem-3-carboxylate

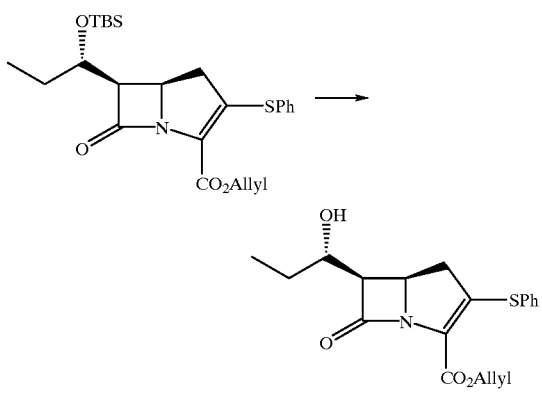

A solution of tetrabutylammonium fluoride (0.42 mmol) and acetic acid (0.036 ml, 0.63 mmol) in N,N-dimethylformamide (0.42 ml) was added to the compound (76 mg, 0.160 mmol) prepared in Example 8 at room temperature in argon atmosphere. The mixture was stirred for 17 hours and diluted with ethyl acetate. The organic layer was washed with a saturated aqueous solution of ammonium chloride and saturated brine in this order, and dried over anhydrous sodium sulfate. The solvent was removed by evaporation under reduced pressure and the residue was purified by silica gel chromatography (hexane/ethyl acetate= 3/1) to obtain 25 mg (yield 43%) of the title compound as a colorless oily substance. 27 mg of the raw material silyl compound was also recovered (recovery rate 36%).

$^1$H-NMR(CDCl$_3$): δ 0.97(3H, t, J=7.3 Hz, CH$_3$CH$_2$CHOH), 1.41–1.86(2H, m, CH$_3$CH$_2$CHOH), 2.52 (1H, dd, J=9.9 and 18.5 Hz, C$_1$—H(H)), 3.11(1H, dd, J=9.2 and 18.5 Hz, C$_1$—H(H) ),3.56(1H, dd, J=5.9 and 8.6 Hz, C$_6$—H), 3.79–3.93(1H, m, CHOH), 4.15(1H, ddd, J=5.9, 9.2 and 9.9 Hz, C$_5$—H), 4.71–4.79(1H, m, CO$_2$CH(H)), 4.82–4.93(1H, m, CO$_2$H(H)), 5.28(1H, dd, J=1.3 and 10.6 Hz, CH=CH(H)), 5.47(1H, dd, J=1.3 and 17.2 Hz, CH=CH(H)), 5.92–6.09(1H, m, CH$_2$CH=CH$_2$), 7.34–7.46(3H, m, Ar), 7.52–7.61(2H, m, Ar)

Example 10

(5R,6R)-2-phenylthio-6-[(S)-1-hydroxypropyl] carbapenem-3-carboxylic acids

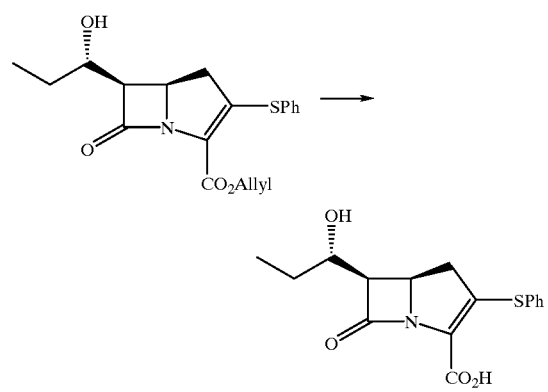

Sodium 2-ethylhexanoate (13.9 mg, 0.083 mmol), triphenyl phosphine (5 mg), and tetrakistriphenyl phosphine palladium (5 mg) were added to a solution of the compound (25 mg, 0.070 mmol) prepared in Example 9 in tetrahydrofuran (0.25 ml) at room temperature in argon atmosphere. After stirring at room temperature for 15 minutes, the mixture was diluted with ether and extracted with water. The water layer was purified by HPLC (ODS, 1 mM ammonium formate, acetonitrile/water) to obtain 5 mg (yield 22%) of the title compound as a colorless solid.

FABMS: 320(M+1), $^1$H-NMR(CD$_3$OD): δ 0.96(3H, t, J=7.3 Hz, CH$_3$CH$_2$CHOH), 1.33–1.46(1H, m, CH$_3$CH(H)CHOH), 1.74–1.85(1H, m, CH$_3$CH(H)CHOH), 2.51(1H, dd, J=9.7 and 17.9 Hz, C$_1$—H(H)), 2.95(1H, dd, J=9.3 and 17.9 Hz, C$_1$—H(H)), 3.50(1H, dd, J=5.7 and 10.0 Hz, C$_6$—H), 3.64–3.72(1H, m), 4.07–4.14(1H, m), 7.35–7.42(3H, m, Ar), 7.53–7.59(2H, m, Ar)

Example 11

Allyl(5R,6R)-2-[(S)-1-allyloxycarbonylpyrrolidine-3-yl]thio-6-[(S)-1-(tert-butyldimethylsilyloxy)propyl]carbapenem-3-carboxylate

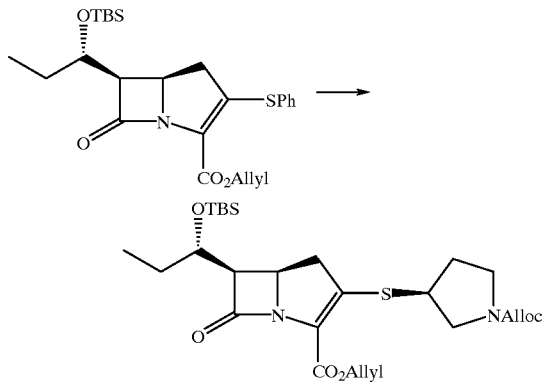

m-Chloroperbenzoic acid (80%, 139 mg, 0.643 mmol) was added to a solution of the compound obtained in Example 8 (210 mg, 0.584 mmol) in methylene chloride (8 ml) at −30° C. in an argon atmosphere. After stirring at this temperature for 50 minutes, the mixture was diluted with ethyl acetate. The organic layer was washed with a saturated aqueous solution of sodium hydrogencarbonate and saturated brine in this order and dried over anhydrous sodium sulfate. The solvent was removed by evaporation under reduced pressure to obtain a sulfoxide compound. To a solution of the sulfoxide compound in N,N-dimethylformamide (15 ml) were added di-isopropylethylamine (0.112 ml, 0,642 mmol) and a solution of (S)-1-allyloxycarbonylpyrrolidine-3-thiol (1.05 mmol) in N,N-dimethylformamide (1.5 ml) at −30° C. After stirring for 30 minutes at this temperature, the mixture was diluted with ethyl acetate. The organic layer was washed with a saturated aqueous solution of sodium hydrogencarbonate and saturated brine in this order. After drying over anhydrous sodium sulfate, the solvent was removed by evaporation under reduced pressure. The residue was purified by silica gel chromatography (hexane/ethyl acetate=4/1) to obtain 277 mg (yield 86%) of the title compound as a colorless oily substance.

IR(neat)cm$^{-1}$: 2928, 1778, 1704, 1698, 1408, 1331

$^1$H-NMR(CDCl$_3$): δ 0.05 and 0.09(total 6H, each s, Si(CH$_3$)$_2$C$_4$H$_9$), 0.84(9H, s, Si(CH$_3$)$_2$C$_4$H$_9$), 0.93(3H, t, J=7.3 Hz, CH$_3$CH$_2$CHOSi), 1.55–1.82(2H, m), 1.89–2.38(3H, m), 2.88–3.00(1H, m), 3.34–3.75(4H, m), 3.78–3.95(1H, m), 4.02–4.36(3H, m), 4.59(2H, d, J=6.0 Hz, CO$_2$CH$_2$), 4.66–4.86(2H, m, CO$_2$CH$_2$), 5.17–5.48(4H, m, CH=CH$_2$), 5.86–6.05(2H, m, CH$_2$CH=CH$_2$)

Example 12

Allyl(5R,6R)-2-[(S)-1-allyloxycarbonylpyrrolidin-3-yl]thio-6-[(S)-1-hydroxypropyl]carbapenem-3-carboxylate

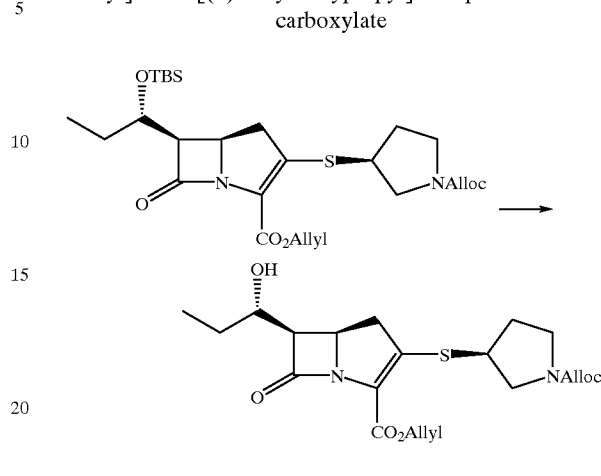

A solution of tetrabutylammonium fluoride (1.01 mmol) and acetic acid (0.086 ml, 1.51 mmol) in N,N-dimethylformamide (0.86 ml) was added to the compound (277 mg, 0.503 mmol) obtained in Example 11 at room temperature in an argon atmosphere, followed by stirring for 17 hours. The mixture was stirred for a further 6 hours at 35° C. The reaction mixture was purified by silica gel chromatography (hexane/ethyl acetate=1/2) to obtain 47 mg (yield 21%) of the title compound as colorless oily substance. In addition, 91 mg (recovery rate: 33%) of the raw material silyl compound was recovered.

$^1$H-NMR(CDCl$_3$): δ 0.96–1.10 (3H, m, CH$_3$CH$_2$CHOH), 1.71–1.92 (2H, m), 1.89–2.06(2H, m), 2.25–2.40(2H, m), 2.86–3.15(2H, m), 3.35–4.05(5H, m), 4.27–4.40(1H, m), 4.58–4.92(4H, m, CO$_2$CH$_2$), 5.20–5.54(4H, m, CH=CH$_2$), 5.88–6.06(2H, m, CH$_2$CH=CH$_2$)

Example 13

(5R,6R)-2-[(S)-pyrrolidin-3-yl]thio-6-[(S)-1-hydroxypropyl]carbapenem-3-carboxylic acid (NH compound) and (5R,6R)-2-[(S)-1-allylpyrrolidin-3-yl]thio-6-[(S)-1-hydroxypropyl]carbapenem-3-carboxylic acid (N-Allyl compound):

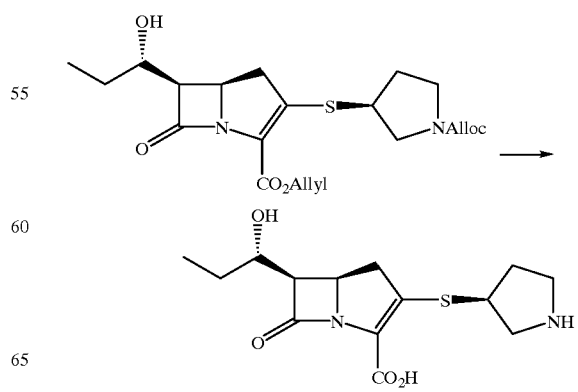

-continued

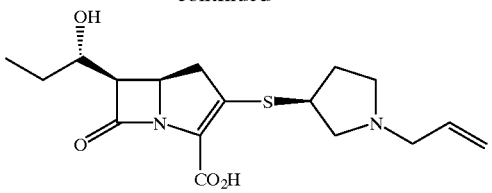

To a solution of the compound (42 mg, 0.096 mmol) obtained in Example 12 in tetrahydrofuran (0.25 ml) were added dimedone (10.1 mg, 0.072 mmol), triphenylphosphine (5 mg), and tetrakistriphenylphosphine palladium (5 mg) at room temperature in an argon atmosphere. After stirring for 10 minutes at room temperature, the mixture was diluted with ether and extracted with water. The water layer was purified by HPLC (ODS, 1 mM ammonium formate, acetonitrile/water) to obtain 10 mg (yield 33%) of the NH compound of the title compound as colorless solid and 5 mg (yield 15%) of the N-allyl compound as a colorless solid.

[NH compound]

IR(KBr)cm$^{-1}$: 3418, 2356, 1751, 1560, 1392

$^1$H-NMR(D$_2$O): δ 0.90–1.02(3H, m, C$\underline{H}_3$CH$_2$CHOH), 1.40–1.62(1H, m), 1.72–1.88(1H, m), 1.99–2.16(1H, m), 2.37–2.60(1H, m), 3.03–3.19(1H, m), 3.25–3.60(4H, m), 3.65–3.80(2H, m), 3.90–4.00(1H, m), 3.98–4.12(1H, m), 4.27–4.38(1H, m)

[N-allyl compound]

IR(KBr)cm$^{-1}$: 3508, 3339, 2946, 1758, 1588, 1394

$^1$H-NMR(D$_2$O): δ 0.98(3H, t, J=7.3 Hz, C$\underline{H}_3$CH$_2$CHOH), 1.42–1.61(1H, m), 1.71–1.90(1H, m), 1.95–2.21(1H, brs), 3.06(1H, dd, J=9.9 and 17.6 Hz, C$_1$—$\underline{H}$(H)), 3.30(1H, dd, J=9.2 and 17.6 Hz, C$_1$—$\underline{H}$(H)), 3.35–3.80(4H, m), 3.84–3.98(2H, m), 4.06–4.17(1H, brs), 4.28–4.37(1H, m), 4.28–4.37(1H, m), 4.65–4.72(2H, m, C$\underline{H}_2$CH=CH,), 5.53–5.62(2H, m, CH=C$\underline{H}_2$), 5.87–5.99(1H, m, CH$_2$C$\underline{H}$=CH$_2$)

Example 14

(5R,6R)-2-[(S)-1-acetoimidoylpyrrolidin-3-yl]thio-6-[(S)-1-hydroxypropyl]carbapenem-3-carboxylic acid

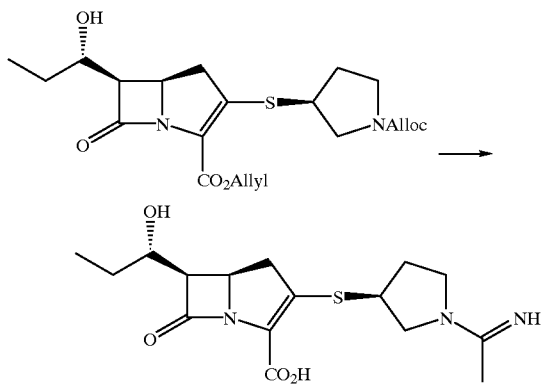

To a solution of the compound (117 mg, 0.27 mmol) prepared in Example 12 in tetrahydrofuran (1.5 ml) were added dimedone (28.2 mg, 0.20 mmol), triphenylphosphine (10 mg), and tetrakistriphenyl phosphine palladium (30 mg) at room temperature in an argon atmosphere. After stirring for 20 minutes at room temperature, a 0.2M phosphate buffer solution (pH=8.2) (15 ml) was added, followed by dropwise addition of an aqueous solution of HBF$_4$ salt of methyl acetoimidate (315 mg, 2.14 mmol, in 5 ml water). The pH of the resulting solution was adjusted to 8.0 with 1N NaOH and the mixture was stirred for 5 minutes, following which the pH was then adjusted to 7.0 with the addition of 1N HCl. After lyophilizing the solution, the residue was purified by HPLC (ODS, 1 mM ammonium formate, acetonitrile/water) to obtain 11 mg (yield 12%) of the title compound as a colorless solid.

IR(KBr)cm$^{-1}$: 3392, 1752, 1685, 1586, 1392

$^1$H-NMR(D$_2$O): δ 0.98(3H, t, J=7.4 Hz), 1.47–1.58(1H, m), 1.72–1.86(1H, m), 2.07–2.23(1H, m), 2.27 and 2.29(3H, each s), 2.45–2.59(1H, m), 3.09–3.18(1H, m) 3.29–3.37(1H, m), 3.46–3.80(4H, m), 3.84–4.11(3H, m), 4.30–4.38(1H, m)

Example 15

Methyl(2R,3S)-2-[(S)-1-(triethylsilyloxy)ethyl]-3-[(R)-1-phenylethyl]amino-5-trimethylsilyl-4-yne carboxylate

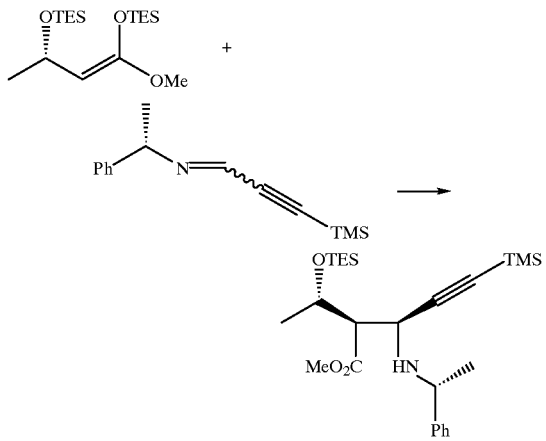

The same reaction as in Example 1 was carried out except that (Z)-1-triethylsilyloxy-1-methoxy-3-(S)-triethylsilyloxy-1-butene (630 mg, 1.82 mmol) was used for imine (219 mg) instead of (Z)-1-triethylsilyloxy-1-methoxy-3-(S)-triethylsilyloxy-1-pentene in the Example 1, to obtain 153 mg (yield 33%) of the title compound.

$^1$H-NMR(CDCl$_3$): δ 0.15(s, 9H),0.57(q, 6H, J=8 Hz), 0.91(t, 9H, J=8 Hz), 1.23(d, 3H, J=6 Hz), 1.31(d, 3H, J=6 Hz), 2.72(dd, 1H, J=8 Hz,5 Hz), 3.67(s, 3H), 3.92(d, 1H, J=5 Hz), 4.05(q, 1H, J=6 Hz), 4.18–4.25(m, 1H), 7.20–7.40(m, 5H)

Example 16

(3R,4S)-3-[(S)-1-(triethylsilyloxy)ethyl]-1-[(R)-1-phenylethyl]-4-[2-(trimethylsilyl)ethynyl]-2-azetidinone

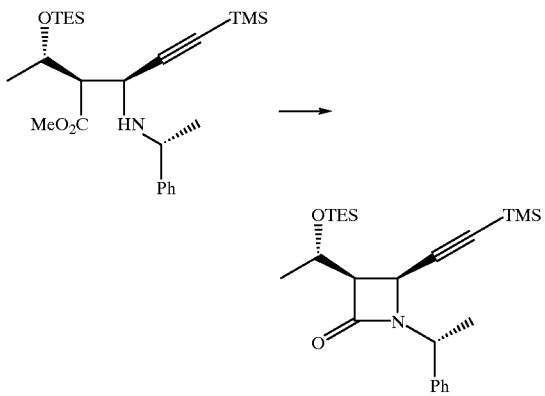

The same reaction as in Example 2 was carried out except that methyl (2R,3S)-2-[(S)-1-(triethylsilyloxy)ethyl]-3-[(R)-1-phenylethyl]amino-5-trimethylsilyl-4-yne carboxylate (75 mg, 0.163 mmol) was used instead of methyl (2R,3S)-2-[(S)-1-(triethylsilyloxy)propyl]-3-[(R)-1-phenylethyl]amino-5-trimethylsilyl-4-yne carboxylate in the Example 2, and, in addition, 0.26 ml (0.16 mmol) of phenyl magnesium bromide (0.634M ether solution) was used, to obtain 32 mg (yield 46%) of the title compound.

$^1$H-NMR(CDCl$_3$): δ 0.09(s, 9H), 0.45–0.58(m, 6H), 0.86 (t, 9H, J=8 Hz), 0.29(d, 3H, 6 Hz), 1.60(d, 3H, J=6 Hz), 3.05(dd, 1H, 5 Hz, 8 Hz), 3.97(d, 1H, J=5 Hz), 4.20–4.30(m, 1H), 4.94(q, 1H, J=7 Hz), 7.20–7.30(m, 5H)

Example 17

(3R,4S)-3-[(S)-1-hydroxyethyl]-1-[(R)-1-phenylethyl]-4-ethynyl-2-azetidinone

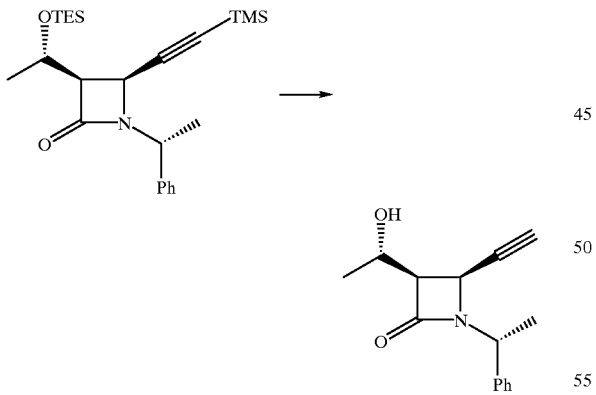

The same reaction as in Example 3 was carried out except that (3R,4S)-3-[(S)-1-(triethylsilyloxy)ethyl]-1-[(R)-1-phenylethyl]-4-[2-(trimethylsilyl)ethynyl]-2-azetidinone (826 mg, 1.92 mmol) was used instead of (3R,4S)-3-[(S)-1-(triethylsilyloxy)propyl]-1-[(R)-1-phenylethyl]-4-[2-(trimethylsilyl)ethynyl]-2-azetidinone in the Example 3, and, in addition 0.28 ml of acetic acid and 4.86 ml (4.76 mmol) of tetrabutylammonium fluoride (1M tetrahydrofuran solution) were used, to obtain 435 mg (yield 93%) of the title compound as colorless oily substance.

$^1$H-NMR(CDCl$_3$): δ 1.42(d, 3H, J=6 Hz), 1.70(d, 3H, J=6 Hz), 2.58(d, 1H, J=2 Hz), 3.16(dd, 1H, J=5 Hz, 9 Hz), 4.04(dd, 1H, J=2 Hz, 5 Hz), 4.29–4.40(m, 1H), 5.05(q, 1H, 7 Hz), 7.30–7.40(m, 5H)

Example 18

(3R,4S)-3-[(S)-1-(tert-butyldimethylsilyloxy)ethyl]-1-[(R)-1-phenylethyl]-4-ethynyl-2-azetidinone

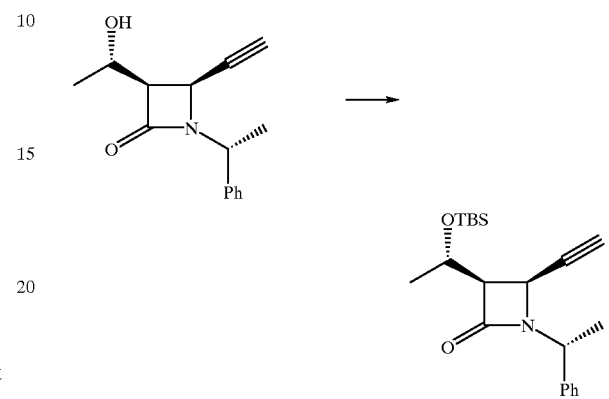

The same reaction as in Example 4 was carried out except that (3R,4S)-3-[(S)-1-hydroxyethyl]-1-[(R)-1-phenylethyl]-4-ethynyl-2-azetidinone (0.435 g, 1.79 mmol) was used instead of (3R,4S)-3-[(S)-1-hydroxypropyl]-1-[(R)-1-phenylethyl]-4-ethynyl-2-azetidinone, to obtain 612 mg (yield 96%) of the title compound as a colorless oily substance.

$^1$H-NMR(CDCl$_3$): δ 0.08(s, 6H), 0.86(s, 9H), 1.37(d, 3H, J=7 Hz), 1.69(d, 3H, J=7 Hz), 2.45(d, 1H, J=3 Hz), 3.15(dd, 1H, J=8 Hz, 6 Hz), 4.01(dd, 1H, J=6 Hz, 3 Hz), 4.30–4.40 (m, 1H), 5.06(q, 1H, 7 Hz), 7.25–7.40(m, 5H)

Example 19

(3R,4S)-3-[(S)-1-(tert-butyldimethylsilyloxy)ethyl]-4-ethynyl-2-azetidinone

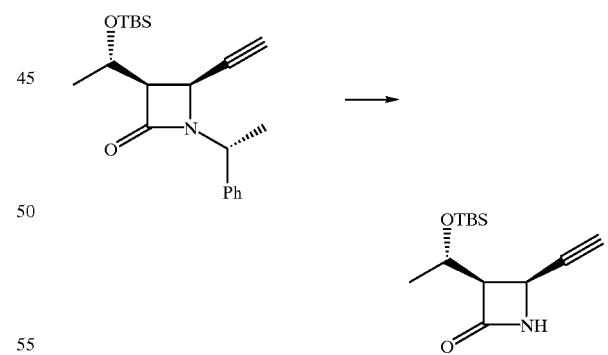

The same reaction as in Example 5 was carried out except that (3R,4S)-3-[(S)-1-(tert-butyldimethylsilyloxy)ethyl]-1-[(R)-1-phenylethyl]-4-ethynyl-2-azetidinone (84 mg, 0.23 mmol) was used instead of (3R,4S)-3-[(S)-1-(tert-butyldimethylsilyloxy)propyl]-1-[(R)-1-phenylethyl]-4-ethynyl-2-azetidinone in the Example 5, to obtain 37 mg (yield 62%) of the title compound.

$^1$H-NMR(CDCl$_3$): δ 0.12(s, 6H), 0.91(s, 9H), 1.42(d, 3H, J=6 Hz), 2.49(d, 1H, J=2 Hz), 3.38–3.45(m, 1H), 4.35–4.42 (m, 2H), 5.9(br. s, 1H)

Example 20

(3R,4S)-3-[(S)-1-(tert-butyldimethylsilyloxy)ethyl)]-4-(2-phenylthioethynyl)-2-azetidinone

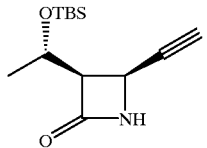

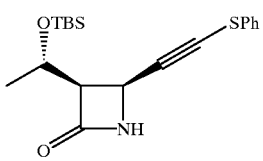

The same reaction as in Example 6 was carried out except that (3R,4S)-3-[(S)-1-(tert-butyldimethylsilyloxy)ethyl]-4-ethynyl-2-azetidinone (37 mg, 0.146 mmol) was used instead of (3R,4S)-3-[(S)-1-(tert-butyldimethylsilyloxy)propyl]-4-ethynyl-2-azetidinone in the Example 6, to obtain 28 mg (yield 53%) of the title compound.

$^1$H-NMR(CDCl$_3$): δ 0.10(s, 6H), 0.89(s, 9H), 1.42(d, 3H, J=6 Hz), 3.42–3.57(m, 1H), 4.38–4.48(m, 1H), 4.66(d, 1H, J=5 Hz), 6.05(br. s, 1H), 7.25–7.50(m, 5H)

Example 21

(3R,4R)-3-[(S)-1-(tert-butyldimethylsilyloxy)ethyl]-4-phenylthiocarbonylmethyl-2-azetidinone

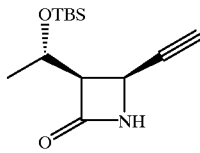

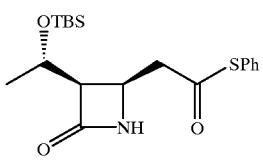

The same reaction as in Example 7 was carried out except that (3R,4S)-3-[(S)-1-(tert-butyldimethylsilyloxy)ethyl]-4-(2-phenylthioethynyl)-2-azetidinone (533 mg, 1.46 g) was used instead of (3R,4S)-3-[(S)-1-(tert-butyldimethylsilyloxy)propyl]-4-(2-phenylthioethynyl)-2-azetidinone in the Example 7, to obtain 379 mg (yield 68%) of the title compound.

$^1$H-NMR(CDCl$_3$): δ 0.15(s, 3H), 0.16(s, 3H), 0.96(s, 9H), 3.25–3.32(m, 1H), 3.32(d, 2H, J=7 Hz), 4.10–4.20(m, 1H), 4.29–4.37(m, 1H), 6.08(br. s, 1H), 7.45(s, 5H)

Example 22

Allyl(5R,6R)-2-phenylthio-6-[(S)-1-(tert-butyldimethylsilyloxy)ethyl]carbapenem-3-carboxylate

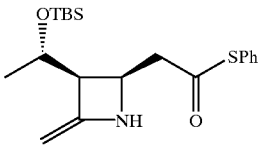

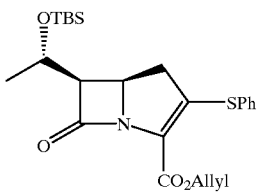

The same reaction as in Example 8 was carried out except that (3R,4R)-3-[(S)-1-(tert-butyldimethylsilyloxy)ethyl]-4-phenylthiocarbonylmethyl-2-azetidinone (326 mg, 0.86 mmol) was used instead of (3R,4R)-3-[(S)-1-(tert-butyldimethyl-silyloxy)propyl]-4-phenylthiocarbonylmethyl-2-azetidinone in the Example 8, to obtain 294 mg (yield 74%) of the title compound.

$^1$H-NMR(CDCl$_3$): δ 0.07(s, 3H), 0.11(s, 3H), 0.84(s, 9H), 1.31(d, 3H, J=6 Hz), 2.49(dd, 1H, J=19 Hz, 8 Hz), 3.24(dd, 1H, J=19 Hz,8 Hz), 3.56(t, 1H, J=6 Hz), 4.14–4.27(m, 2H), 4.78–4.95(m, 2H), 5.34(d, 1H, J=10 Hz), 5.55(d, 1H, J=7 Hz), 6.02–6.15(m, 1H), 7.40–7.55(m, 3H), 7.60–7.67(m, 2H)

Example 23

Allyl(5R,6R)-2-phenylthio-6-[(S)-1-hydroxyethyl]carbapenem-3-carboxylate

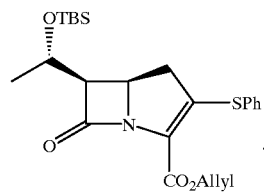

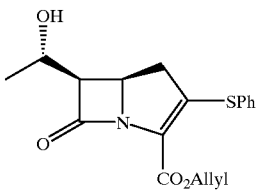

The same reaction as in Example 9 was carried out except that allyl(5R,6R)-2-phenylthio-6-[(S)-1-(tert-butyldimethylsilyloxy)ethyl]carbapenem-3-carboxylate (294 mg, 0.64 mmol) was used instead of allyl(5R,6R)-2-phenylthio-6-[(S)-1-(tert-butyldimethylsilyloxy)propyl]carbapenem-3-carboxylate in the Example 9, to obtain 138 mg (yield 62%) of the title compound. In addition, 46 mg (recovery 15%) of the raw material silyl compound was recovered.

$^1$H-NMR(CDCl$_3$): δ 1.34(d, 3H, J=6 Hz), 2.53(dd, 1H, J=10 Hz, 18 Hz), 3.07(dd, 1H, J=10 Hz, 18 Hz), 3.49(dd,

1H, J=8 Hz, 6 Hz), 4.05–4.20(m, 2 H), 4.73(dd, 1H, J=5 Hz, 13 Hz), 4.85(dd, 1H, J=5 Hz, 13 Hz), 5.27(d, 1H, J=10 Hz), 5.48(d, 1H, J=17 Hz), 5.95–6.04(m, 1H), 7.55–7.45(m, 3H), 7.55–7.60(m, 2H)

Example 24

Allyl(5R,6R)-2-[(S)-1-allyloxycarbonylpyrrolidin-3-yl]thio-6-[(S)-1-hydroxyethyl]carbapenem-3-carboxylate

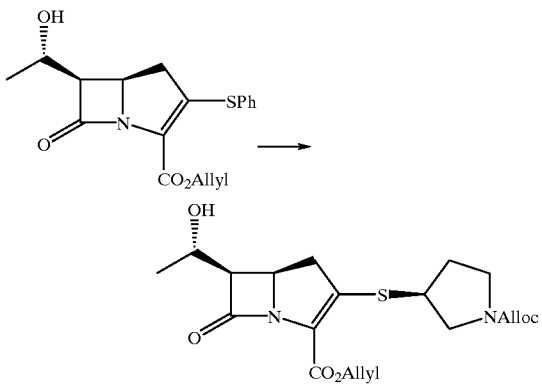

The same reaction as in Example 11 was carried out except that allyl(5R,6R)-2-phenylthio-6-[(S)-1-hydroxyethyl]carbapenem-3-carboxylate (138 mg, 0.40 mmol) was used instead of allyl(SR,6R)-2-phenylthio-6-[(S)-1-(tert-butyldimethylsilyloxy)propyl]carbapenem-3-carboxylate in the Example 11, to obtain 75 mg (yield 44%) of the title compound.

$^1$H-NMR(CDCl$_3$): δ 1.41(d, 3H, J=8 Hz), 1.90–2.08(m, 1H), 2.27–2.38(m, 1H), 3.06(dd, 1H,J=10 Hz, 18 Hz), 3.45–3.63(m, 4H), 3.70–3.80(m, 1H), 3.85–3.95(m, 1H), 4.15–4.25(m, 1H), 4.25–4.40(m, 1H), 4.55–4.65(m, 2H), 4.65–4.85(m, 2H), 5.20–5.45(m, 3H), 5.44(d, 1H, J=7 Hz), 5.90–6.05(m, 2H)

Example 25

(5R,6R)-2-[(S)-pyrrolidin-3-yl]thio-6-[(S)-1-hydroxyethyl]carbapenem-3-carboxylic acid (NH compound) and (5R,6R)-2-[(S)-1-allylpyrrolidin-3-yl]thio-6-[(S)-1-hydroxyethyl]carbapenem-3-carboxylicacid (N-allyl compound)

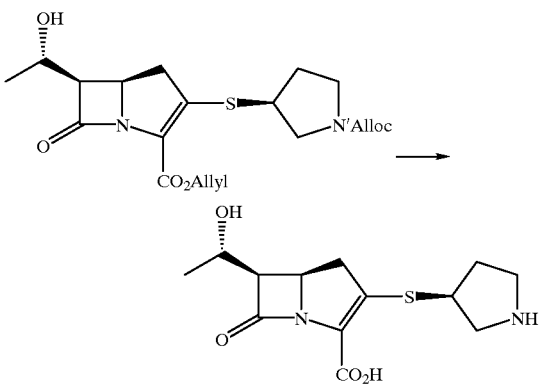

-continued

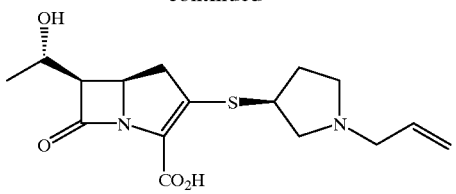

The same reaction as in Example 13 was carried out except that allyl(5R,6R)-2-[(S)-1-allyloxycarbonylpyrrolidin-3-yl]thio-6-[(S)-1-hydroxyethyl]carbapenem-3-carboxylate (37 mg, 0,088 mmol) was used instead of allyl(5R,6R)-2-[(S)-1-allyloxycarbonylpyrrolidin-3-yl]thio-$^6$-[(S)-1-hydroxypropyl]carbapenem-3-carboxylate in the Example 13, to obtain 10 mg (yield 38%) of the NH compound and 3 mg (yield 10%) of the N-allyl compound, respectively, of the title compound.

[NH compound]
IR(KBr)cm$^{-1}$: 1752, 1400
$^1$H-NMR(D$_2$O): δ 1.48(d, 1H, J=6 Hz), 2.15–2.28(m, 1H), 2.60–2.70(m, 1H), 3.25(dd, 1H, J=10 Hz, 18 Hz), 3.40–3.60(m, 3H),3.65–3.72(m, 1H), 3.80–3.90(m, 2H), 4.15–4.23(m, 1H), 4.25–4.35(m, 1H), 4.40–4.50(m, 1H)

[N-allyl compound]
$^1$H-NMR(D$_2$O): δ 1.35(d, 3H, J=6 Hz), 2.0–2.2(m, 1H), 2.60–2.75(m, 1H), 3.10(dd, 1H, J=10 Hz, 18 Hz), 3.30(dd, 1H, J=10 Hz, 18 Hz), 3.65–3,75(m, 1H), 3.4–4.0(br. m. 4H), 3.90(d, 2H, J=7 Hz), 4.0–4.4(m, 3H), 5.55–5.7(m, 2H), 5.85–6.05(m, 1H)

Example 26

Allyl(5R,6R)-2-[(3S,5S)-1-allyloxycarbonyl-5-(N,N-dimethylcarbamoyl)pyrrolidin-3-yl]thio-6-[(S)-1-(tert-butyldimethylsilyloxy)propyl]carbapenem-3-carboxylate

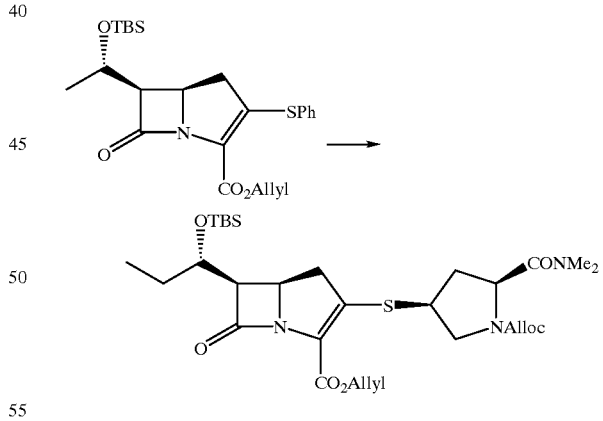

The same reaction as in Example 11 was carried out except that allyl(5R,6R)-2-phenylthio-6-[(S)-1-(tert-butyldimethylsilyloxy)propyl]carbapenem-3-carboxylate was used in an amount of 151 mg (0.42 mmol) and, instead of (S)-1-allyloxycarbonylpyrrolidine-3-thiol in the Example 11, (3S,5S)-1-allyloxycarbonyl-5-(N,N-dimethylcarbamoyl)pyrrolidine-3-thiol (184 mg, 0.67 mmol) was used. 170 mg (yield 65%) of the title compound in the form of a colorless oily substance was obtained.

$^1$H-NMR(CDCl$_3$): δ 0.05 and 0.09 (total 6H, each s), 0.84(9H, s), 0.88–0.96(3H, m), 1.55–1.80(2H, m), 1.88–2.05(1H, m), 2.50–2.65(1H, m) 2.84–3.14(8H, m), 3.41–3.61(3H, m), 3.97–4.23(2H, m), 4.47–4.62(2H, m), 4.65–4.82(4H, m), 5.15–5.45(4H, m), 5.84–6.02(2H, m)

Example 27

Allyl(5R,6R)-2-[(3S,5S)-1-allyloxycarbonyl-5-(N,N-dimethylcarbamoyl)]pyrrolidin-3-yl]thio-6-[(S)-1-hydroxypropyl]carbapenem-3-carboxylate

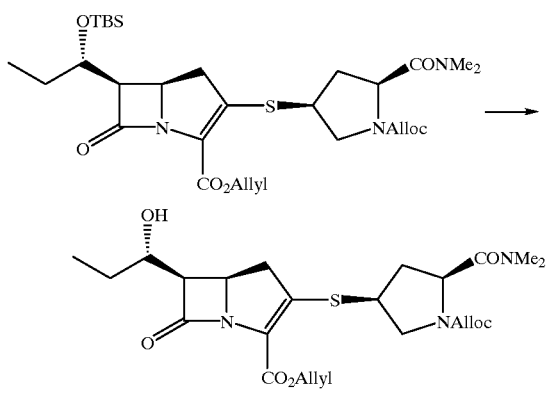

The same reaction as in Example 9 was carried out except that allyl(5R,6R)-2-[(3S,5 S)-1-allyloxycarbonyl-5-(N,N-dimethylcarbamoyl)pyrrolidin-3-yl]thio-6-[(S)-1-(tert-butyldimethylsilyloxy)propyl]carbapenem-3-carboxylate (170 mg, 0.27 mmol) was used instead of allyl(5R,6R)-2-phenylthio-6-[(S)-1-(tert-butyldimethylsilyloxy)propyl]carbapenem-3-carboxylate, to obtain 40 mg (yield 29%) of the title compound as a yellow oily substance.

$^1$H-NMR(CDCl$_3$): δ 0.84–1.11(3H, m), 1.30–2.10(3H, m), 2.30–2.51(1H, m), 2.62–2.77(1H, m), 2.90–3.22(7H, m), 3.45–3.78(3H, m), 3.92–4.40(2H, m), 4.88–7.88(6H, m), 5.15–5.52(4H, m), 5.80–6.05(2H, m)

Example 28

(5R,6R)-2-[(3S,5S)-1-allyl-5-(N,N-dimethylcarbamoyl)pyrrolidin-3-yl]thio-6-[(S)-1-hydroxypropyl]carbapenem-3-carboxylic acid

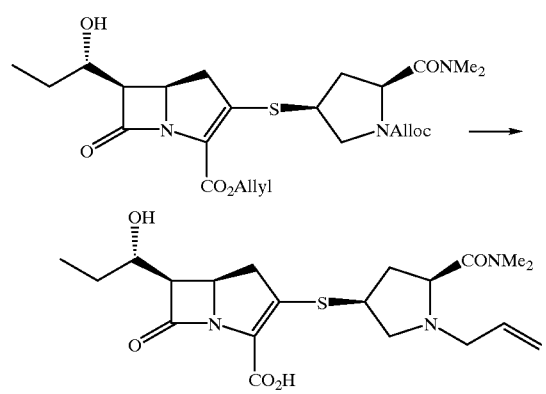

The same reaction as in Example 13 was carried out except that allyl(5R,6R)-2-[(3S,5S)-1-allyloxycarbonyl-5-(N,N-dimethylcarbamoyl)pyrrolidin-3-yl]thio-6-[(S)-1-hydroxypropyl]carbapenem-3-carboxylate (41 mg, 0.081 mmol) was used instead of allyl(5R,6R)-2-[(S)-1-allyloxycarbonylpyrrolidin-3-yl]thio-6-[(S)-1-hydroxypropyl]carbapenem-3-carboxylate in the Example 13, to obtain 6 mg (yield 18%) of the title compound as a colorless solid.

IR(KBr)cm$^{-1}$: 3394, 1756, 1653, 1406

$^1$H-NMR(D$_2$O): δ 0.98(3H, t, J=7.3 Hz), 1.45–1.59(1H, m), 1.72–1.87(1H, m), 1.96–2.08(1H, m), 2.99(3H, s), 3.05 (3H, s), 3.03–3.35(3H, m), 3.71–3.98(7H, m), 4.16–4.25 (1H, m), 4.29–4.36(1H, m), 5.50–5.63(2H, m), 5.82–5.95 (1H, m)

Example 29

Allyl(5R,6R)-2-[(S)-1-phenacylpyrrolidin-3-yl]thio-6-[(S)-1-hydroxypropyl]carbapenem-3-carboxylate

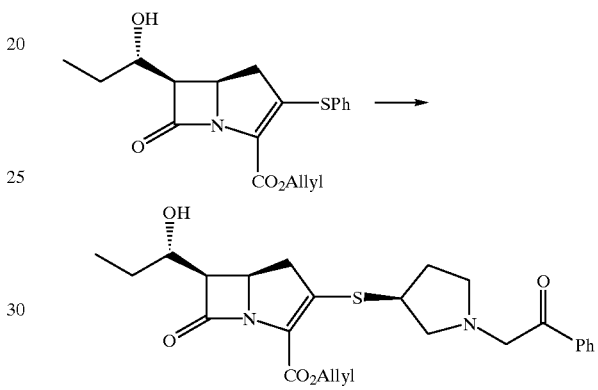

The same reaction as in Example 11 was carried out except that allyl(5R,6R)-2-phenylthio-6-[(S)-1-hydroxypropyl]carbapenem-3-carboxylate (63 mg, 0.17 mmol) was used instead of allyl(5R,6R)-2-phenylthio-6-[(S)-1-(tert-butyldimethylsilyloxy)propyl]carbapenem-3-carboxylate and (S)-1-phenacylpyrrolidin-3-thiol (44 mg, 0.20 mmol) was used instead of (S)-1-allyloxycarbonylpyrrolidine-3-thiol, to obtain 38 mg (yield 46%) of the title compound as yellow oily substance.

$^1$H-NMR(CDCl$_3$): δ 1.02(3H, t, J=7.3 Hz), 1.48–1.68(1H, m), 1.77–1.94(2H, m), 2.38–2.49(1H, m), 2.58(1H, dd, J=6.9 and 9.6 Hz), 2.65–2.75(1H, m), 2.98–3.12(2H, m), 3.40–3.48(1H, m), 3.75–3.68(2H, m), 3.72–3.81(1H, m), 3.90–3.99(1H, m), 4.02(2H, brs), 4.23–4.30(1H, m), 4.65–4.72(1H, m), 4.77–4.84(1H, m), 5.23–5.28(1H, m), 5.41–5.48(1H, m), 5.91–6.04(1H, m), 7.43–7.52(2H, m), 7.56–7.61(1H, m), 7.94–8.00(2H, m)

Example 30

(5R,6R)-2-[(S)-1-phenacylpyrrolidin-3-yl]thio-6-[(S)-1-hydroxypropyl]carbapenem-3-carboxylic acid

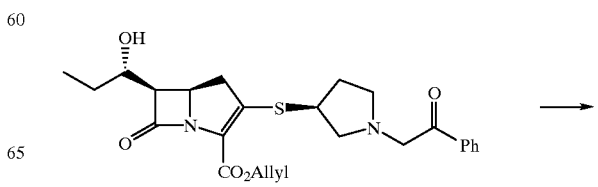

-continued

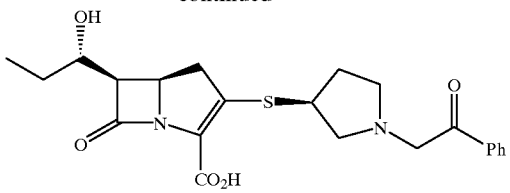

The same reaction as in Example 13 was carried out except that allyl(5R,6R)-2-[(S)-1-phenacylpyrrolidin-3-yl]thio-6-[(S)-1-hydroxypropyl]carbapenem-3-carboxylate (20 mg, 0.053 mmol) was used instead of allyl(5R,6R)-2-[(S)-1-allyloxycarbonylpyrrolidin-3-yl]thio-6-[(S)-1-hydroxypropyl]carbapenem-3-carboxylate in the Example 13, to obtain 3.6 mg (yield 22%) of the title compound as a colorless solid.

IR(KBr)cm$^{-1}$: 3421,1755,1694,1597,1394

$^1$H-NMR(D$_2$O): δ 0.98(3H, t, J=7.3 Hz), 1.48–1.58(1H, m), 1.75–1.87(1H, m), 2.07–2.20(1H, m), 2.58–2.70(1H, m), 3.05–3.15(2H, m), 3.29–3.38(2H, m), 3.40–3.54(2H, m), 3.57–3.67(1H, m), 3.75(1H, dd, J=5.4 and 9.6 Hz), 3.80–3.89(1H, m), 3.92–3.99(1H, m), 4.06–4.15(1H, m), 4.30–4.37(1H, m), 7.60–7.67(2H, m), 7.75–7.82(1H, m), 7.98–8.04(2H, m)

Example 31

(3R,4R)-3-[(S)-1-(triethylsilyloxy)propyl]-4-phenylthiocarbonylmethyl-2-azetidinone

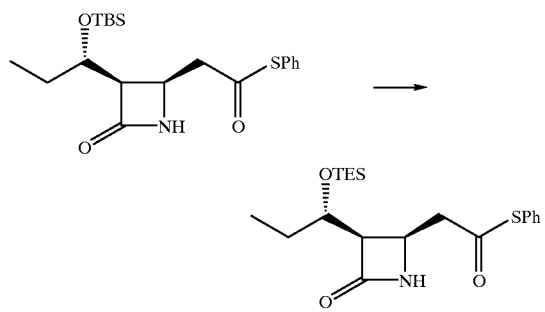

An aqueous solution of hydrogen fluroride (46%, 2.53 ml) was added to a solution of the compound (2.29 g, 5.8 mmol) prepared in Example 7 in acetonitrile (40 ml) at room temperature in an argon atmosphere. After stirring for two hours at this temperature, the mixture was diluted with ethyl acetate, washed with a saturated aqueous solution of sodium hydrogencarbonate and saturated brine in this order, and dried over anhydrous sodium sulfate. The solvent was evaporated under reduced pressure to obtain a de-protected compound as an oily substance. Imidazole (579 mg, 8.5 mmol) and triethylsilyl chloride (1.24 ml, 7.4 mmol) were added to the solution of this de-protected compound in N,N-dimethylformamide (10 ml) at room temperature, followed by stirring for 10 minutes at the same temperature. After the reaction, the reaction mixture was diluted with ethyl acetate, washed with a saturated aqueous solution of potassium hydrogen sulfate, a saturated aqueous solution of sodium hydrogencarbonate, and saturated brine in this order, and dried over anhydrous sodium sulfate. The solvent was evaporated under reduced pressure and the residue was purified by silica gel chromatography (hexane/ethyl acetate=3/1), to obtain 1.52 g (yield 67%) of the title compound as a light yellow oily substance.

$^1$H-NMR(CDCl$_3$): δ 0.67(6H, q, J=7.8 Hz), 0.93(3H, t, J=7.5 Hz), 1.00(9H, t, J=7.8 Hz), 1.52–1.78(2H, m), 3.22 (1H, dd, J=2.9 and 6.7 Hz), 3.37–3.48(2H, m), 4.07–4.20 (2H, m), 6.02(1H, brs), 7.39–7.50(5H, m)

Example 32

Allyl(5R,6R)-2-phenylthio-6-[(S)-1-(triethylsilyloxy)propyl]carbapenem-3-carboxylate

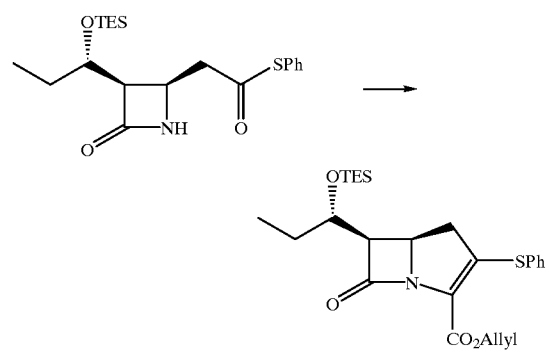

The same reaction as in Example 8 was carried out except that (3R,4R)-3-[(S)-1-(triethylsilyloxy)propyl]-4-phenylthiocarbonylmethyl-2-azetidinone (1.52 g, 3.87 mmol) was used instead of (3R,4R)-3-[(S)-1-(tert-butyldimethyl silyloxy)propyl]-4-phenylthiocarbonylmethyl-2-azetidinone in the example 8, to obtain 950 mg (yield 52%) of the title compound as a yellow oily substance.

$^1$H-NMR(CDCl$_3$): δ 0.51(6H, q, J=7.8 Hz), 0.81–0.96 (12H, m), 1.48–1.70(2H, m), 2.37(1H, dd, J=10.0 and 18.2 Hz), 3.34(1H, dd, J=9.0 and 18.2 Hz), 3.59–3.65(1H, m), 4.02–4.14(2H, m), 5.72–5.90(2H, m), 5.23–5.31(1H, m), 5.45–5.53(1H, m), 5.94–6.08(1H, m), 7.32–7.48(3H,m), 7.53–7.60(2H, m)

Example 33

Allyl(5R,6R)-2-(1-allyloxycarbonylpiperidin-4-yl)thio-6-[(S)-1-(triethylsilyloxy)propyl]carbapenem-3-carboxylate

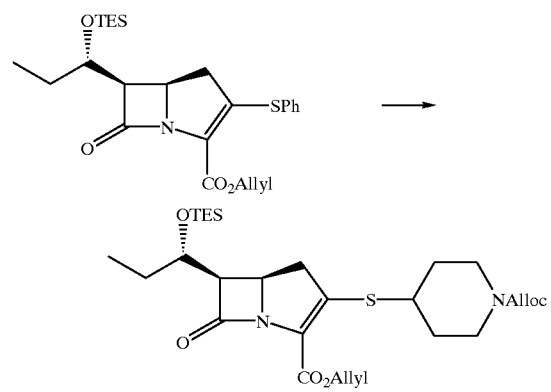

The same reaction as in Example 11 was carried out except that allyl(5R,6R)-2-phenylthio-6-[(S)-1-(triethylsilyloxy)propyl]carbapenem-3-carboxylate (104 mg, 0.21 mmol) was used instead of allyl(5R,6R)-2-phenylthio-6-[(S)-1-(tert-butyldimethylsilyloxy)propyl]carbapenem-3-carboxylate and 1-allyloxycarbonylpiperidine-4-thiol (74 mg, 0.37 mmol) was used instead of (S)-1-allyloxycarbonylpyrrolidine-3-thiol, to obtain 81 mg (yield 67%) of the title compound as an yellow oily substance.

$^1$H-NMR(CDCl$_3$): δ 0.59(6H, q, J=8.0 Hz), 0.88–0.98 (12H, m), 1.48–1.79(2H, m), 1.93–2.05(4H, m), 2.86–3.12 (4H, m), 3.92–4.28(5H, m), 4.55–4.61(2H, m), 4.68–4.73 (1H, m), 4.77–4.84(2H, m), 5.18–5.32(4H, m), 5.88–6.02 (2H, m)

Example 34

Allyl(5R,6R)-2-(1-allyloxycarbonylpiperidin-4-yl)thio-6-[(S)-1-hydroxypropyl]carbapenem-3-carboxylate

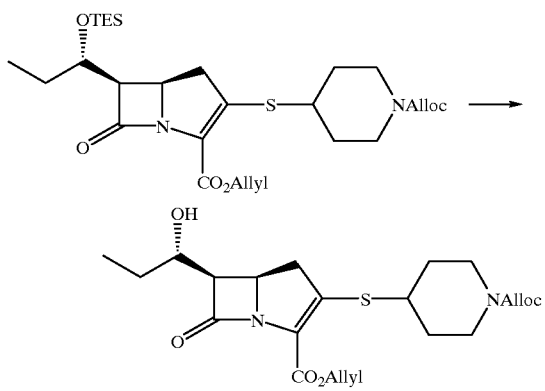

The same reaction as in Example 9 was carried out except that allyl(5R,6R)-2-(1-allyloxycarbonylpiperidin-4-yl)thio-6-[(S)-1-(triethylsilyloxy)propyl]carbapenem-3-carboxylate (81 mg, 0.14 mmol) was used instead of allyl (5R,6R)-2-phenylthio-6-[(S)-1-(tert-butyldimethylsilyloxy) propyl]carbapenem-3-carboxylate in Example 9, to obtain 43 mg (yield 67%) of the title compound as a yellow oily substance.

IR(neat)cm$^{-1}$: 3446, 2931, 1778, 1699, 1278

$^1$H-NMR(CDCl$_3$): δ 0.84–0.95(3H, m), 1.48–1.92(2H, m), 1.95–2.08(2H, m), 2.28–2.38(2H, m), 3.03–3.15(3H, m), 3.20–3.31(1H, m), 3.53–3.66(3H, m), 3.92–4.06(1H, m), 4.17–4.33(2H, m), 4.55–4.62(2H, m), 4.63–4.71(1H, m), 4.77–4.84(1H, m), 5.17–5.33(3H, m), 5.40–5.48(1H, m), 5.86–6.01(2H, m)

Example 35

(5R,6R)-2-(4-piperidinyl)thio-6-[(S)-1-hydroxypropyl]carbapenem-3-carboxylic acid

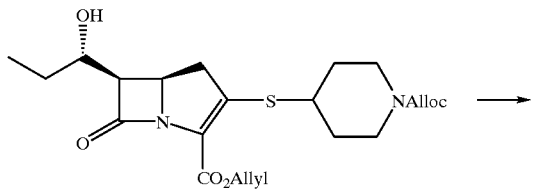

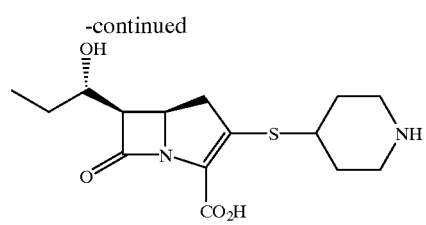

The same reaction as in Example 13 was carried out except that allyl(5R,6R)-2-(1-allyloxycarbonylpiperidin-4-yl)thio-6-[(S)-1-hydroxypropyl]carbapenem-3-carboxylate (39 mg, 0.083 mmol) was used instead of allyl(5R,6R)-2-[(S)-1-allyloxycarbonylpyrrolidin-3-yl]thio-6-[(S)-1-hydroxypropyl]carbapenem-3-carboxylate, to obtain 3 mg (yield of the title compound a colorless solid.

IR(KBr)cm$^{-1}$: 3412, 1751, 1598, 1540, 1393

$^1$H-NMR(D$_2$O): δ 0.98(3H, t, J=7.3 Hz), 1.48–1.60(1H, m), 1.74–1.92(3H, m), 2.19–2.34(2H, m), 3.10–3.33(4H, m), 3.44–3.56(3H, m), 3.72–3.80(1H, m), 3.92–4.00(1H, m), 4.28–4.36(1H, m)

Obviously, numerous modifications and variations of the present invention are possible in light of the above teachings. It is therefore to be understood that, within the scope of the appended claims, the invention may be practiced otherwise than as specifically described herein.

What is claimed is:

1. A carbapenem derivative represented by the formula:

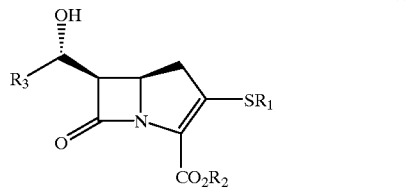

(I)

wherein $R_1$ is a substituted or unsubstituted aryl or a substituted or unsubstituted, saturated heteromonocyclic group selected from the group consisting of azetidinyl, pyrrolidinyl, imidazolidinyl, piperidinyl, pyrazolidinyl and piperazinyl; $R_2$ is hydrogen or $CO_2R_2$ is an esterified carboxy group and $R^3$ is methyl or ethyl; or a pharmaceutically acceptable salt thereof.

2. The carbapenem derivative of claim 1, wherein $R_1$ is a substituted or unsubstituted, saturated hetero-monocyclic group selected from the group consisting of azetidinyl, pyrrolidinyl, imidazolidinyl, piperidinyl, pyrazolidinyl and piperazinyl.

3. A pharmaceutical composition comprising as an active ingredient a carbapenem derivative of formula (I):

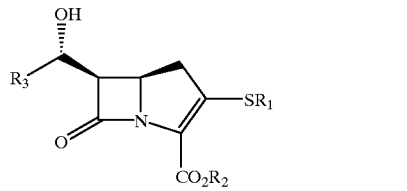

(I)

wherein $R_1$ is a substituted or unsubstituted aryl or substituted or unsubstituted, saturated heteromonocyclic group selected from the group consisting of azetidinyl, pyrrolidinyl, imidazolidinyl, piperidinyl, pyrazolidinyl and piperazinyl, $R_2$ is hydrogen or $CO_2R_2$ is an esterified carboxy group and $R_3$ is methyl or ethyl; or a pharmaceutically acceptable salt thereof.

4. The carbapenem derivative according to claim 2, wherein said $R_1$ group is pyrrolidinyl.

5. The carbapenem derivative according to claim 2, wherein said $R_1$ group is (S)-pyrrolidin-3-yl.

6. The carbapenem derivative of claim 1, wherein $R_1$ is substituted or unsubstituted aryl.

7. The carbapenem derivative according to claim 6, wherein the aryl group is a $C_{6-10}$ aryl group.

8. The carbapenem derivative according to claim 6, wherein said aryl group is phenyl, tolyl, xylyl, mesityl, cumenyl or naphthyl.

9. A compound of formula (II):

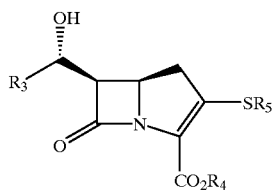

(II)

wherein $R_3$ is methyl or ethyl, $CO_2R_4$ is an esterified carboxy group, $R_5$ is a substituted or unsubstituted aryl or a substituted or unsubstituted, saturated hetero-monocyclic group selected from the group consisting of azetidinyl, pyrrolidinyl, imidazolidinyl, piperidinyl, pyrazolidinyl and piperazinyl.

10. A compound of formula (III):

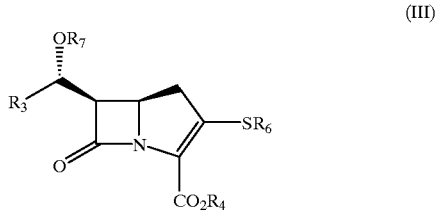

(III)

wherein $R_3$ is methyl or ethyl, $CO_2R_4$ is an esterified carboxy group, $R_6$ is a substituted or unsubstituted aryl or a substituted or unsubstituted, saturated heteromonocyclic group selected from the group consisting of azetidinyl, pyrrolidinyl, imidazolidinyl, piperidinyl, pyrazolidinyl and piperazinyl, and $OR_7$ is a protected hydroxyl group.

11. The pharmaceutical composition according to claim 3, wherein the composition is effective against methicillin-resistant *Staphylococcus aureus*.

* * * * *